United States Patent [19]
Quail et al.

[11] Patent Number: 6,020,190
[45] Date of Patent: *Feb. 1, 2000

[54] PLANT UBIQUITIN PROMOTER SYSTEM

[75] Inventors: Peter H. Quail, Richmond; Alan H. Christensen, Albany, both of Calif.; Howard P. Hershey, West Chester, Pa.; Robert A. Sharrock, El Cerrito, Calif.; Thomas D. Sullivan, Madison, Wis.

[73] Assignee: Mycogen Plant Science, Inc., San Diego, Calif.

[*] Notice: This patent is subject to a terminal disclaimer.

[21] Appl. No.: 08/746,822

[22] Filed: Nov. 18, 1996

Related U.S. Application Data

[62] Division of application No. 08/462,092, Jun. 5, 1995, Pat. No. 5,614,399, which is a division of application No. 08/296,268, Aug. 25, 1994, Pat. No. 5,510,474, which is a continuation of application No. 08/191,134, Feb. 3, 1994, abandoned, which is a continuation of application No. 08/076,363, Jun. 11, 1993, abandoned, which is a continuation of application No. 07/670,496, Mar. 15, 1991, abandoned, which is a continuation of application No. 07/194,824, May 17, 1988, abandoned.

[51] Int. Cl.[7] ............................ C12N 15/29; C12N 15/82; A01H 4/00; A01H 5/00

[52] U.S. Cl. .................. 435/320.1; 435/419; 435/468; 435/69.1; 536/24.1; 536/23.6; 800/298

[58] Field of Search .................. 536/24.1, 23.6; 435/69.1, 172.3, 320.1, 468, 419; 800/205, 298

[56] References Cited

U.S. PATENT DOCUMENTS 5,510,474  4/1996  Quail et al. ............................ 536/24.1

*Primary Examiner*—Douglas W. Robinson
*Assistant Examiner*—Thomas Haas
*Attorney, Agent, or Firm*—Saliwanchik, Lloyd & Saliwanchik

[57] ABSTRACT

A method of inducibly enhancing the constitutive expression of a DNA sequence of interest is described in which plant cells are transformed with a DNA sequence of interest that is operably joined to a plant ubiquitin regulatory region comprised of a heat shock element, a promoter, a transcription start site, an intron and a translation start site, When monocot or dicot plant cells are subjected to permissive heat shock temperatures, the level of expression of the DNA sequence of interest is enhanced.

1 Claim, 11 Drawing Sheets

```
                                      -890            -870            -850
                                        .      .       .       .       .
                                        CTGCAGTGCAGCGTGACCCGGTCGTGCCCCTCTCTAGAGATAATGAGCATTGCATGTCTA
                                                -830            -810            -790
                                                  .       .       .       .       .
                                                  AGTTATAAAAATTACCACATATTTTTTTGTCACACTGTTTGAAGTGCAGTTTATCTA
                                                        -770            -750            -730
                                                          .       .       .       .       .
                                                          TCTTTATACATATATTTAAACTTTACTCTACGAATAATAATCTATAGTACTACAATAA
                                                                -710            -690            -670
                                                                  .       .       .       .       .
                                                                  TATCAGTGTTTTAGAGAATCATATAAATGAACAGTTAGACATGGTCTAAAGGACAATTGA
                                                                        -650            -630            -610
                                                                          .       .       .       .       .
                                                                          GTATTTTGACAACAGGACTCTACAGTTTTATCTTTTTAGTGTGCATGTGTTCTCCTTTT
                                                                                -590            -570            -550
                                                                                  .       .       .       .       .
                                                                                  TTTTGCAAATAGCTTCACCTATATAATACTTCATCCATTTTATTAGTACATCCATTTAGG
                                                                                        -530            -510            -490
                                                                                          .       .       .       .       .
                                                                                          GTTTAGGGTTTAATGGTTTTTATAGACTAATTTTTTTAGTACACATCTATTTTATTCTATTTT
                                                                                                -470            -450            -430
                                                                                                  .       .       .       .       .
                                                                                                  AGCCTCTAAATTAAGAAAACTAAAACTCTATTTTAGTTTTTTTATTTTAATAATTTAGATA
                                                                                                        -410            -390            -370
                                                                                                          .       .       .       .       .
                                                                                                          TAAAATAGAATAAAAATAAGTGACTAAAAATTAAACAAATACCCTTTAAGAAATTAAAAA
                                                                                                                -350            -330            -310
                                                                                                                  .       .       .       .       .
                                                                                                                  AACTAAGGAAACATTTTCTTGTTTCGAGTAGATAATGCCAGCCTGTAAACGCCGTCGA
                                                                                                                        -290            -270            -250
                                                                                                                          .       .       .       .       .
                                                                                                                          CGAGTCTAACGGACACCAACCAGCGAACCAGCAGCGTCGGTCGGCCAAGGCGAAGCAGA
```

FIG. 2-A

```
                                                          .                          .
CGGCACGGCATCTCTGTCGCTGCCTCTGGACCCCCTCTCGAGAGTTCCGCTCCACCGTGG
       -230                 -210                 -190               -170                 -150                 -130
                      .                          .                          .
ACTTGCTCCGCTGTCGGCATCCAGAAATTGGTGGGAGCGGCAGACGTGAGCCGGCAC
              -110                  -90                  -70
                      .                          .                          .
GGCAGGGCGGCCCTCCTCCTCTCACGGCACGGCAGCTACGGGGGATTCCTTTCCCACCG
               -50                   -30                   -10
                      .                          .                          .
CTCCTTCGCTTTCCCTTCCTCCGCCCGCCCGTAATAAATAGACACCCCCTCCACACCCTCTT
                10                    30                    50
                      .                          .                          .
TCCCCAACCTCGTGTTCGGAGCGCACACACAACAACCAGATCTCCCCCAAATCCAC
                70                    90                   110
                      .                          .                          .
CCGTCGGCACCTCCGCTTCAAGGTACGCCCGTCCTCCTCCCCCCCCCCTCTCTACCT
              130                  150                  170
                      .                          .                          .
TCTCTAGATCGGCGTTCCGGTCCATGGTTAGGGCCCGGTAGTTCTACTTCTGTTCATGTT
              190                  210                  230
                      .                          .                          .
TGTGTTAGATCCGTGTTTGTGTGTTAGATCCGTGCTGCTACGGTTCGTACACGGATGCGACC
              250                  270                  290
                      .                          .                          .
TGTACGTCTCAGACACGTTCTGATTGCTAACTTGCCAGTGTTTCTCTTGGGAATCCTGGG
              310                  330                  350
                      .                          .                          .
ATGGCTCTAGCCCGTTCCGCAGACGGGATCGATTTCATGATTTTTTTTGTTTCGTTGCATA
              370                  390                  410
                      .
GGGTTTGGTTTGCCCTTTTCCTTTATTTCAATATATGCCGTGCACTTGTTTGTCGGGTCA
```

```
                        430                 450                 470
TCTTTTCATGCTTTTTTTTGTCTTGGTTGTGATGATGTGGTCTGGTTGGGCGGGTCGTTCT
            490                 510                 530
AGATCGGAGTAGAATTCTGTTTCAAACTACCTGGTGGATTTATTAATTTTGGATCTGTAT
            550                 570                 590
GTGTGTGCCATACATATTCATAGTTACGAATTGAAGATGATGGAAATATCGATCTA
            610                 630                 650
GGATAGGTATACATGTTGATGCGGGTTTTACTGATGCATATACAGAGATGCTTTTTGTTC
            670                 690                 710
GCTTGGTTGTGATGATGTGGTGGTGTTGGGCGGTCGTTCATTCGTTCTAGATCGGAGTAG
            730                 750                 770
AATACTGTTTCAAACTACCTGGTGTATTTATTAATTTTGGAACTGTATGTGTGTCATA
            790                 810                 830
CATCTTCATAGTTACGAGTTTAAGATGGATGGAAATATCGATCTAGGATAGGTATACATG
            850                 870                 890
TTGATGTGGGTTTTACTGATGCATATACATGATGGCATATGCAGCATCTATTCATATGCT
            910                 930                 950
CTAACCCTGAGTACCTATCTATTATAATAAACAAGTATGTTTTATAATTATTTTGATCTT
            970                 990                 1010
GATATACTTGGATGATGGCATATGCAGCAGCTATATGTGGATTTTTTTAGCCCTGCCTTC
            1030                1050                1070
ATACGCTATTTATTTGCTTGGTACTGTTTCTTTTGTCGATGCTCACCCTGTTGTTTGGTG
```

Figure 2:
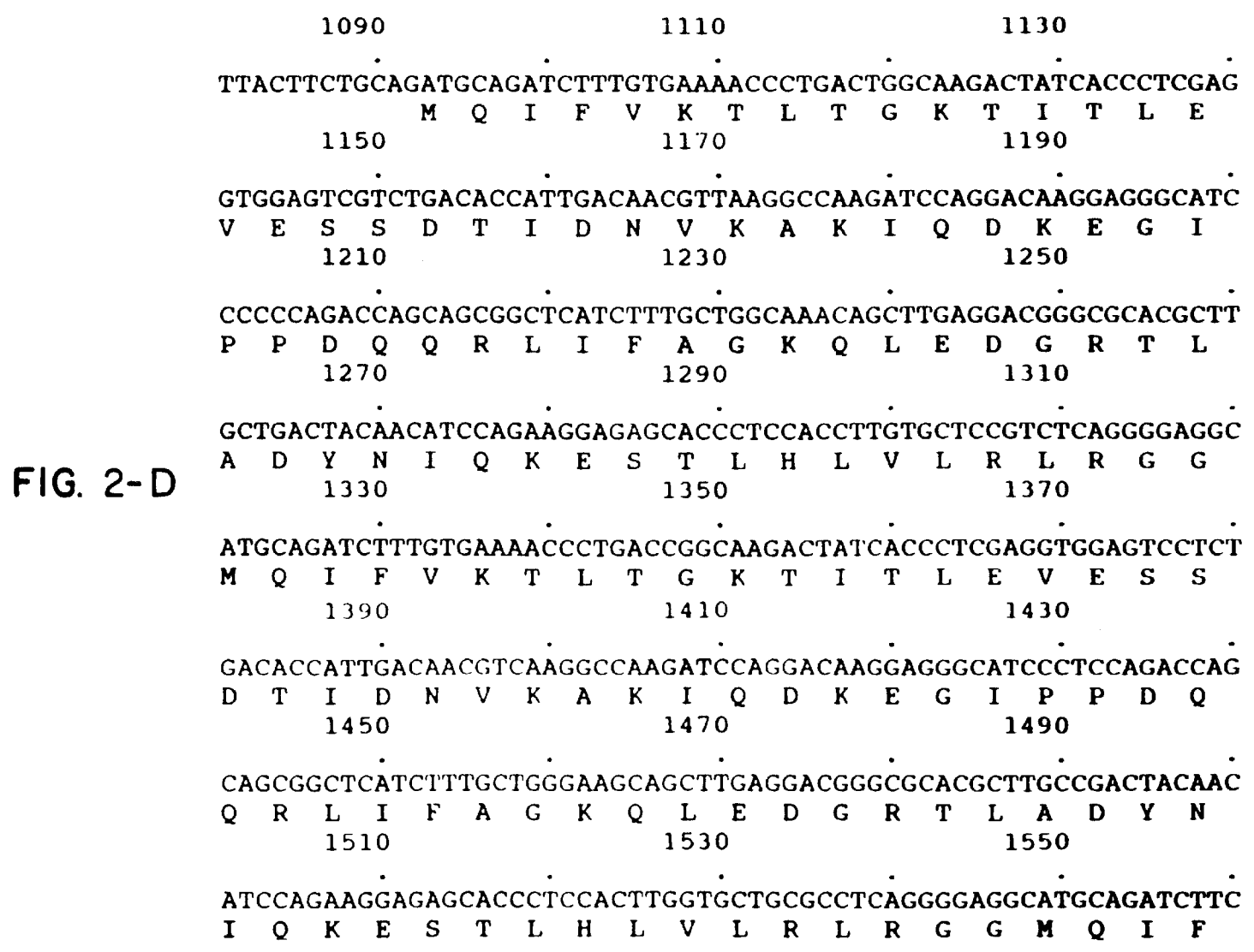

```
                                                                                     1130
       1090                     1110
TTACTTCTGCAGATGCAGATCTTTGTGAAACCCTGACTGGCAAGACTATCACCCTCGAG
        M  Q  I  F  V  K  T  L  T  G  K  T  I  T  L  E
       1150                     1170                     1190
GTGGAGTCGTCTGACAACCATTGACACGTTAAGGCCAAGATCCAGGACAAGGAGGCATC
 V  E  S  S  D  T  I  D  N  V  K  A  K  I  Q  D  K  E  G  I
       1210                     1230                     1250
CCCCCAGACCAGCAGCGGCTCATCTTTGCTGGCAAACAGTTGAGGACGGCCACGCTT
 P  P  D  Q  Q  R  L  I  F  A  G  K  Q  L  E  D  G  R  T  L
       1270                     1290                     1310
GCTGACTACAACATCCAGAAGGAGAGCACCCTCCACTTGTCTCCGTCTCAGGGGAGGC
 A  D  Y  N  I  Q  K  E  S  T  L  H  L  V  L  R  L  R  G  G
       1330                     1350                     1370
ATGCAGATCTTTGTGAAACCCTGACCGGCAAGACTATCACCCTCGAGTGGAGTCCTCT
 M  Q  I  F  V  K  T  L  T  G  K  T  I  T  L  E  V  E  S  S
       1390                     1410                     1430
GACACCATTGACAACGTCAAGGCCAAGATCCAGGACAAGGAGGGCATCCCTCCAGACCAG
 D  T  I  D  N  V  K  A  K  I  Q  D  K  E  G  I  P  P  D  Q
       1450                     1470                     1490
CAGCGGCTCATCTTTGCTGGGAAGCAGCTTGAGGACGGGCGCACGCTTGCCGACTACAAC
 Q  R  L  I  F  A  G  K  Q  L  E  D  G  R  T  L  A  D  Y  N
       1510                     1530                     1550
ATCCAGAAGGAGAGCACCCTCCACTTGGTGCTGCGCCTCAGGGGAGGCATGCAGATCTTC
 I  Q  K  E  S  T  L  H  L  V  L  R  L  R  G  G  M  Q  I  F
```

FIG. 2-D

```
                                             1590                                                    1610
GTGAAGACCCTGACCGGCAAGACTATCACCCTCGAGTGGAGTCTTCAGACACCATCGAC
 V  K  T  L  T  G  K  T  I  T  L  E  V  E  S  S  D  T  I  D
              1630                                    1650                                    1670

AACGTCAAGGCCAAGATCCAGGACAAGGAGGGCATTCCCCCAGACCAGCAGCGGCTCATC
 N  V  K  A  K  I  Q  D  K  E  G  I  P  P  D  Q  Q  R  L  I
              1690                                    1710                                    1730

TTTGCTGGAAAGCAGCTTGAGGACGGGCGCACGCTTGCCGACTACAACATCCAGAAGGAG
 F  A  G  K  Q  L  E  D  G  R  T  L  A  D  Y  N  I  Q  K  E
              1750                                    1770                                    1790

AGCACCCTCCACTTGGTCTGCCCTCAGGGAGGCATGCAGATCTTCGTGAAGACCCTG
 S  T  L  H  L  V  L  R  L  R  G  G  M  Q  I  F  V  K  T  L
              1810                                    1830                                    1850

ACCGGCAAGACTATCACCCTCGAGTGGAGTCTTCAGACACCATCGACAATGTCAAGGCC
 T  G  K  T  I  T  L  E  V  E  S  S  D  T  I  D  N  V  K  A
              1870                                    1890                                    1910

AAGATCCAGGACAAGGAGGGCATCCCACCGGACCAGCAGCGTTTGATCTTCGCTGGCAAG
 K  I  Q  D  K  E  G  I  P  P  D  Q  Q  R  L  I  F  A  G  K
              1930                                    1950                                    1970

CAGCTGGAGGATGGCCGCACCCTTGCGGATTACAACATCCAGAAGGAGAGCACCCTCCAC
 Q  L  E  D  G  R  T  L  A  D  Y  N  I  Q  K  E  S  T  L  H
              1990                                    2010                                    2030

CTGGTGCTCCGTCTCAGGGGTGGTATGCAGATCTTTGTGAAGACACTCACTGGCAAGACA
 L  V  L  R  L  R  G  G  M  Q  I  F  V  K  T  L  T  G  K  T
```

```
                                      2050                    2070                     2090
ATCACCCTTGAGGTGGAGTCTTCGGATACCATTGACAATGTCAAGGCCAAGATCCAGGAC
 I  T  L  E  V  E  S  S  D  T  I  D  N  V  K  A  K  I  Q  D
                                      2110                    2130                    2150
AAGGAGGGCATCCCACCCGACCAGCAGCGCCTCATCTTCGCCGGCAAGCAGTGGAGGAT
 K  E  G  I  P  P  D  Q  Q  R  L  I  F  A  G  K  Q  L  E  D
                                      2170                    2190                    2210
GGCCGCACCCTGGCGGATTACAACATCCAGAAGGAGAGCACTCTCCACCTGGTGCTCCGC
 G  R  T  L  A  D  Y  N  I  Q  K  E  S  T  L  H  L  V  L  R
                                      2230                    2250                    2270
CTCAGGGGTGGCATGCAGATTTTTGTGAAGACATTGACTGGCAAGACCATCACCTTGGAG
 L  R  G  G  M  Q  I  F  V  K  T  L  T  G  K  T  I  T  L  E
                                      2290                    2310                    2330
GTGGAGAGCTCTGACACCATTGACAATGTGAAGGCCAAGATCCAGGACAAGGAGGGCATT
 V  E  S  S  D  T  I  D  N  V  K  A  K  I  Q  D  K  E  G  I
                                      2350                    2370                    2390
CCCCCAGACCAGCAGCGTCTGATCTTTGCGGGCAAGCAGCTGGAGGATGGCCGCACTCTC
 P  P  D  Q  Q  R  L  I  F  A  G  K  Q  L  E  D  G  R  T  L
                                      2410                    2430                    2450
GCGGACTACAACATCCAGAAGGAGCACCCTTCACCTTGTTCTCCGCCTCAGAGGTGGT
 A  D  Y  N  I  Q  K  E  S  T  L  H  L  V  L  R  L  R  G  G
                                      2470                    2490                    2510
ATGCAGATCTTTGTAAAGACCCTGACTGGAAAAACCATAACCCTGGAGGTTGAGAGCTCG
 M  Q  I  F  V  K  T  L  T  G  K  T  I  T  L  E  V  E  S  S
```

```
GACACCATCGACAATGTGAAGGCGAAGATCCAGGACAAGGAGGGCATCCCCCCGGACCAG
 D  T  I  D  N  V  K  A  K  I  Q  D  K  E  G  I  P  P  D  Q
            2590                    2610                    2630

CAGGCGTCTGATCTTCGCCGGCAAACAGCTGGAGGATGGCCGCACCCTAGCAGACTACAAC
 Q  R  L  I  F  A  G  K  Q  L  E  D  G  R  T  L  A  D  Y  N
            2650                    2670                    2690

ATCCAAAAGGAGAGCACCCTCCACCTTGTGCTCCGTCTCCGTGGTGTCAGTAAGTCATG
 I  Q  K  E  S  T  L  H  L  V  L  R  L  R  G  G  Q
            2710                    2730                    2750

GGTCGTTAAGCTGCCGATGTGCCTGGTCGTCGTGCCCTCTCTCCATATGGAGGTTG
            2770                    2790                    2810

TCAAAGTATCTGCTGTTCCGTCGTTCATGAGTCGTGTTGGTTTAATAATGGACCGGT
            2830                    2850                    2870

TGTGTTGTGTGTGCCTACCCAGAACTATGACAAATCATGAATAAGTTTGATGTTTGA
            2890                    2910                    2930

AATTAAAGCCTGTGCTGCTCATTATGTTCTGTCTTTCAGTTGTCTCCCTAATATTTGCCTGCAG
```

FIG. 2-G

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 3840 base pairs
      (B) TYPE: nucleic acid

```
        (C) STRANDEDNESS: single
        (D) TOPOLOGY: linear (ii) MOLECULE TYPE: DNA (genomic)

(ii) MOLECULE TYPE: DNA (genomic)

(ix) FEATURE:
        (A) NAME/KEY: CDS
        (B) LOCATION: 1993..3591

(xi) SEQUENCE DESCRIPTION: SEQ ID NO:1:

CTGCAGTGCA GCGTGACCCG GTCGTGCCCC TCTCTAGAGA TAATGAGCAT TGCATGTCTA      60

AGTTATAAAA AATTACCACA TATTTTTTTT GTCACACTTG TTTGAAGTGC AGTTTATCTA     120

TCTTTATACA TATATTTAAA CTTTACTCTA CGAATAATAT AATCTATAGT ACTACAATAA     180

TATCAGTGTT TTAGAGAATC ATATAAATGA ACAGTTAGAC ATGGTCTAAA GGACAATTGA     240

GTATTTTGAC AACAGGACTC TACAGTTTTA TCTTTTTAGT GTGCATGTGT TCTCCTTTTT     300

TTTTGCAAAT AGCTTCACCT ATATAATACT TCATCCATTT TATTAGTACA TCCATTTAGG     360

GTTTAGGGTT AATGGTTTTT ATAGACTAAT TTTTTTAGTA CATCTATTTT ATTCTATTTT     420

AGCCTCTAAA TTAAGAAAAC TAAAACTCTA TTTTAGTTTT TTTATTTAAT AATTTAGATA     480

TAAAATAGAA TAAAATAAAG TGACTAAAAA TTAAACAAAT ACCCTTTAAG AAATTAAAAA     540

AACTAAGGAA ACATTTTTCT TGTTTCGAGT AGATAATGCC AGCCTGTTAA ACGCCGTCGA     600

CGAGTCTAAC GGACACCAAC CAGCGAACCA GCAGCGTCGC GTCGGGCCAA GCGAAGCAGA     660

CGGCACGGCA TCTCTGTCGC TGCCTCTGGA CCCCTCTCGA GAGTTCCGCT CCACCGTTGG     720

ACTTGCTCCG CTGTCGGCAT CCAGAAATTG CGTGGCGGAG CGGCAGACGT GAGCCGGCAC     780

GGCAGGCGGC CTCCTCCTCC TCTCACGGCA CGGCAGCTAC GGGGGATTCC TTTCCCACCG     840

CTCCTTCGCT TTCCCTTCCT CGCCCGCCGT AATAAATAGA CACCCCCTCC ACACCCTCTT     900

TCCCCAACCT CGTGTTGTTC GGAGCGCACA CACACACAAC CAGATCTCCC CCAAATCCAC     960

CCGTCGGCAC CTCCGCTTCA AGGTACGCCG CTCGTCCTCC CCCCCCCCCC CTCTCTACCT    1020

TCTCTAGATC GGCGTTCCGG TCCATGGTTA GGGCCCGGTA GTTCTACTTC TGTTCATGTT    1080

TGTGTTAGAT CCGTGTTTGT GTTAGATCCG TGCTGCTAGC GTTCGTACAC GGATGCGACC    1140

TGTACGTCAG ACACGTTCTG ATTGCTAACT TGCCAGTGTT TCTCTTTGGG GAATCCTGGG    1200

ATGGCTCTAG CCGTTCCGCA GACGGGATCG ATTTCATGAT TTTTTTTGTT TCGTTGCATA    1260

GGGTTTGGTT TGCCCTTTTC CTTTATTTCA ATATATGCCG TGCACTTGTT TGTCGGGTCA    1320

TCTTTTCATG CTTTTTTTTG TCTTGGTTGT GATGATGTGG TCTGGTTGGG CGGTCGTTCT    1380

AGATCGGAGT AGAATTCTGT TTCAAACTAC CTGGTGGATT TATTAATTTT GGATCTGTAT    1440

GTGTGTGCCA TACATATTCA TAGTTACGAA TTGAAGATGA TGGATGGAAA TATCGATCTA    1500

GGATAGGTAT ACATGTTGAT GCGGGTTTTA CTGATGCATA TACAGAGATG CTTTTTGTTC    1560

GCTTGGTTGT GATGATGTGG TGTGGTTGGG CGGTCGTTCA TTCGTTCTAG ATCGGAGTAG    1620

AATACTGTTT CAAACTACCT GGTGTATTTA TTAATTTTGG AACTGTATGT GTGTGTCATA    1680

CATCTTCATA GTTACGAGTT TAAGATGGAT GGAAATATCG ATCTAGGATA GGTATACATG    1740

TTGATGTGGG TTTTACTGAT GCATATACAT GATGGCATAT GCAGCATCTA TTCATATGCT    1800

CTAACCTTGA GTACCTATCT ATTATAATAA ACAAGTATGT TTTATAATTA TTTTGATCTT    1860

GATATACTTG GATGATGGCA TATGCAGCAG CTATATGTGG ATTTTTTTAG CCCTGCCTTC    1920

ATACGCTATT TATTTGCTTG GTACTGTTTC TTTTGTCGAT GCTCACCCTG TTGTTTGGTG    1980
```

-continued

```
TTACTTCTGC AG ATG CAG ATC TTT GTG AAA ACC CTG ACT GGC AAG ACT        2028
          Met Gln Ile Phe Val Lys Thr Leu Thr Gly Lys Thr
           1               5                   10

ATC ACC CTC GAG GTG GAG TCG TCT GAC ACC ATT GAC AAC GTT AAG GCC       2076
Ile Thr Leu Glu Val Glu Ser Ser Asp Thr Ile Asp Asn Val Lys Ala
            15                  20                  25

AAG ATC CAG GAC AAG GAG GGC ATC CCC CCA GAC CAG CAG CGG CTC ATC       2124
Lys Ile Gln Asp Lys Glu Gly Ile Pro Pro Asp Gln Gln Arg Leu Ile
        30                  35                  40

TTT GCT GGC AAA CAG CTT GAG GAC GGG CGC ACG CTT GCT GAC TAC AAC       2172
Phe Ala Gly Lys Gln Leu Glu Asp Gly Arg Thr Leu Ala Asp Tyr Asn
    45                  50                  55                  60

ATC CAG AAG GAG AGC ACC CTC CAC CTT GTG CTC CGT CTC AGG GGA GGC       2220
Ile Gln Lys Glu Ser Thr Leu His Leu Val Leu Arg Leu Arg Gly Gly
                65                  70                  75

ATG CAG ATC TTT GTG AAA ACC CTG ACC GGC AAG ACT ATC ACC CTC GAG       2268
Met Gln Ile Phe Val Lys Thr Leu Thr Gly Lys Thr Ile Thr Leu Glu
            80                  85                  90

GTG GAG TCC TCT GAC ACC ATT GAC AAC GTC AAG GCC AAG ATC CAG GAC       2316
Val Glu Ser Ser Asp Thr Ile Asp Asn Val Lys Ala Lys Ile Gln Asp
        95                  100                 105

AAG GAG GGC ATC CCT CCA GAC CAG CAG CGG CTC ATC TTT GCT GGG AAG       2364
Lys Glu Gly Ile Pro Pro Asp Gln Gln Arg Leu Ile Phe Ala Gly Lys
    110                 115                 120

CAG CTT GAG GAC GGG CGC ACG CTT GCC GAC TAC AAC ATC CAG AAG GAG       2412
Gln Leu Glu Asp Gly Arg Thr Leu Ala Asp Tyr Asn Ile Gln Lys Glu
125                 130                 135                 140

AGC ACC CTC CAC TTG GTG CTG CGC CTC AGG GGA GGC ATG CAG ATC TTC       2460
Ser Thr Leu His Leu Val Leu Arg Leu Arg Gly Gly Met Gln Ile Phe
                145                 150                 155

GTG AAG ACC CTG ACC GGC AAG ACT ATC ACC CTC GAG GTG GAG TCT TCA       2508
Val Lys Thr Leu Thr Gly Lys Thr Ile Thr Leu Glu Val Glu Ser Ser
            160                 165                 170

GAC ACC ATC GAC AAC GTC AAG GCC AAG ATC CAG GAC AAG GAG GGC ATT       2556
Asp Thr Ile Asp Asn Val Lys Ala Lys Ile Gln Asp Lys Glu Gly Ile
        175                 180                 185

CCC CCA GAC CAG CAG CGG CTC ATC TTT GCT GGA AAG CAG CTT GAG GAC       2604
Pro Pro Asp Gln Gln Arg Leu Ile Phe Ala Gly Lys Gln Leu Glu Asp
    190                 195                 200

GGG CGC ACG CTT GCC GAC TAC AAC ATC CAG AAG GAG AGC ACC CTC CAC       2652
Gly Arg Thr Leu Ala Asp Tyr Asn Ile Gln Lys Glu Ser Thr Leu His
205                 210                 215                 220

TTG GTG CTG CGC CTC AGG GGA GGC ATG CAG ATC TTC GTG AAG ACC CTG       2700
Leu Val Leu Arg Leu Arg Gly Gly Met Gln Ile Phe Val Lys Thr Leu
                225                 230                 235

ACC GGC AAG ACT ATC ACC CTC GAG GTG GAG TCT TCA GAC ACC ATC GAC       2748
Thr Gly Lys Thr Ile Thr Leu Glu Val Glu Ser Ser Asp Thr Ile Asp
            240                 245                 250

AAT GTC AAG GCC AAG ATC CAG GAC AAG GAG GGC ATC CCA CCG GAC CAG       2796
Asn Val Lys Ala Lys Ile Gln Asp Lys Glu Gly Ile Pro Pro Asp Gln
        255                 260                 265

CAG CGT TTG ATC TTC GCT GGC AAG CAG CTG GAG GAT GGC CGC ACC CTT       2844
Gln Arg Leu Ile Phe Ala Gly Lys Gln Leu Glu Asp Gly Arg Thr Leu
    270                 275                 280

GCG GAT TAC AAC ATC CAG AAG GAG AGC ACC CTC CAC CTG GTG CTC CGT       2892
Ala Asp Tyr Asn Ile Gln Lys Glu Ser Thr Leu His Leu Val Leu Arg
285                 290                 295                 300
```

```
CTC AGG GGT GGT ATG CAG ATC TTT GTG AAG ACA CTC ACT GGC AAG ACA         2940
Leu Arg Gly Gly Met Gln Ile Phe Val Lys Thr Leu Thr Gly Lys Thr
                    305                 310                 315

ATC ACC CTT GAG GTG GAG TCT TCG GAT ACC ATT GAC AAT GTC AAG GCC         2988
Ile Thr Leu Glu Val Glu Ser Ser Asp Thr Ile Asp Asn Val Lys Ala
                320                 325                 330

AAG ATC CAG GAC AAG GAG GGC ATC CCA CCC GAC CAG CAG CGC CTC ATC         3036
Lys Ile Gln Asp Lys Glu Gly Ile Pro Pro Asp Gln Gln Arg Leu Ile
            335                 340                 345

TTC GCC GGC AAG CAG CTG GAG GAT GGC CGC ACC CTG GCG GAT TAC AAC         3084
Phe Ala Gly Lys Gln Leu Glu Asp Gly Arg Thr Leu Ala Asp Tyr Asn
        350                 355                 360

ATC CAG AAG GAG AGC ACT CTC CAC CTG GTG CTC CGC CTC AGG GGT GGC         3132
Ile Gln Lys Glu Ser Thr Leu His Leu Val Leu Arg Leu Arg Gly Gly
365                 370                 375                 380

ATG CAG ATT TTT GTG AAG ACA TTG ACT GGC AAG ACC ATC ACC TTG GAG         3180
Met Gln Ile Phe Val Lys Thr Leu Thr Gly Lys Thr Ile Thr Leu Glu
                    385                 390                 395

GTG GAG AGC TCT GAC ACC ATT GAC AAT GTG AAG GCC AAG ATC CAG GAC         3228
Val Glu Ser Ser Asp Thr Ile Asp Asn Val Lys Ala Lys Ile Gln Asp
                400                 405                 410

AAG GAG GGC ATT CCC CCA GAC CAG CAG CGT CTG ATC TTT GCG GGC AAG         3276
Lys Glu Gly Ile Pro Pro Asp Gln Gln Arg Leu Ile Phe Ala Gly Lys
            415                 420                 425

CAG CTG GAG GAT GGC CGC ACT CTC GCG GAC TAC AAC ATC CAG AAG GAG         3324
Gln Leu Glu Asp Gly Arg Thr Leu Ala Asp Tyr Asn Ile Gln Lys Glu
430                 435                 440

AGC ACC CTT CAC CTT GTT CTC CGC CTC AGA GGT GGT ATG CAG ATC TTT         3372
Ser Thr Leu His Leu Val Leu Arg Leu Arg Gly Gly Met Gln Ile Phe
445                 450                 455                 460

GTA AAG ACC CTG ACT GGA AAA ACC ATA ACC CTG GAG GTT GAG AGC TCG         3420
Val Lys Thr Leu Thr Gly Lys Thr Ile Thr Leu Glu Val Glu Ser Ser
                    465                 470                 475

GAC ACC ATC GAC AAT GTG AAG GCG AAG ATC CAG GAC AAG GAG GGC ATC         3468
Asp Thr Ile Asp Asn Val Lys Ala Lys Ile Gln Asp Lys Glu Gly Ile
                480                 485                 490

CCC CCG GAC CAG CAG CGT CTG ATC TTC GCC GGC AAA CAG CTG GAG GAT         3516
Pro Pro Asp Gln Gln Arg Leu Ile Phe Ala Gly Lys Gln Leu Glu Asp
            495                 500                 505

GGC CGC ACC CTA GCA GAC TAC AAC ATC CAA AAG GAG AGC ACC CTC CAC         3564
Gly Arg Thr Leu Ala Asp Tyr Asn Ile Gln Lys Glu Ser Thr Leu His
        510                 515                 520

CTT GTG CTC CGT CTC CGT GGT GGT CAG TAAGTCATGG GTCGTTTAAG              3611
Leu Val Leu Arg Leu Arg Gly Gly Gln
525                 530

CTGCCGATGT GCCTGCGTCG TCTGGTGCCC TCTCTCCATA TGGAGGTTGT CAAAGTATCT      3671

GCTGTTCGTG TCATGAGTCG TGTCAGTGTT GGTTTAATAA TGGACCGGTT GTGTTGTGTG      3731

TGCGTACTAC CCAGAACTAT GACAAATCAT GAATAAGTTT GATGTTTGAA ATTAAAGCCT      3791

GTGCTCATTA TGTTCTGTCT TTCAGTTGTC TCCTAATATT TGCCTGCAG                 3840

(2) INFORMATION FOR SEQ ID NO:2:

(i) SEQUENCE CHARACTERISTICS:
        (A) LENGTH: 533 amino acids
        (B) TYPE: amino acid
        (D) TOPOLOGY: linear (ii) MOLECULE TYPE: protein
```

(xi) SEQUENCE DESCRIPTION: SEQ ID NO:2:

```
Met Gln Ile Phe Val Lys Thr Leu Thr Gly Lys Thr Ile Thr Leu Glu
  1               5                  10                  15

Val Glu Ser Ser Asp Thr Ile Asp Asn Val Lys Ala Lys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ala Asp Tyr Asn Ile Gln Lys Glu
     50                  55                  60

Ser Thr Leu His Leu Val Leu Arg Leu Arg Gly Gly Met Gln Ile Phe
 65                  70                  75                  80

Val Lys Thr Leu Thr Gly Lys Thr Ile Thr Leu Glu Val Glu Ser Ser
                 85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
    210                 215                 220

Leu Arg Gly Gly Met Gln Ile Phe Val Lys Thr Leu Thr Gly Lys Thr
225                 230                 235                 240

Ile Thr Leu Glu Val Glu Ser Ser Asp Thr Ile Asp Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ala Asp Tyr Asn
        275                 280                 285

Ile Gln Lys Glu Ser Thr Leu His Leu Val Leu Arg Leu Arg Gly Gly
    290                 295                 300

Met Gln Ile Phe Val Lys Thr Leu Thr Gly Lys Thr Ile Thr Leu Glu
305                 310                 315                 320

Val Glu Ser Ser Asp Thr Ile Asp Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ala Asp Tyr Asn Ile Gln Lys Glu
        355                 360                 365

Ser Thr Leu His Leu Val Leu Arg Leu Arg Gly Gly Met Gln Ile Phe
    370                 375                 380

Val Lys Thr Leu Thr Gly Lys Thr Ile Thr Leu Glu Val Glu Ser Ser
385                 390                 395                 400
```

-continued

```
Asp Thr Ile Asp Asn Val Lys Ala Lys Ile Gln Asp Lys Glu Gly Ile
            405                 410                 415

Pro Pro Asp Gln Gln Arg Leu Ile Phe Ala Gly Lys Gln Leu Glu Asp
            420                 425                 430

Gly Arg Thr Leu Ala Asp Tyr Asn Ile Gln Lys Glu Ser Thr Leu His
            435                 440                 445

Leu Val Leu Arg Leu Arg Gly Gly Met Gln Ile Phe Val Lys Thr Leu
        450                 455                 460

Thr Gly Lys Thr Ile Thr Leu Glu Val Glu Ser Ser Asp Thr Ile Asp
465                 470                 475                 480

Asn Val Lys Ala Lys Ile Gln Asp Lys Glu Gly Ile Pro Pro Asp Gln
            485                 490                 495

Gln Arg Leu Ile Phe Ala Gly Lys Gln Leu Glu Asp Gly Arg Thr Leu
            500                 505                 510

Ala Asp Tyr Asn Ile Gln Lys Glu Ser Thr Leu His Leu Val Leu Arg
            515                 520                 525

Leu Arg Gly Gly Gln
        530
```

PLANT UBIQUITIN PROMOTER SYSTEM

CROSS REFERENCE TO RELATED APPLICATIONS

This is a division of application Ser. No. 08/462,092, filed Jun. 5, 1995 now U.S. Pat. No. 5,614,399, which is a division of application Ser. No. 08/296,268, filed Aug. 25, 1994 (now U.S. Pat. No. 5,510,474), which is a continuation of application Ser. No. 08/191,134, filed Feb. 3, 1994 (now abandoned), which is a continuation of application Ser. No. 08/076,363, filed Jun. 11, 1993 (now abandoned), which is a continuation of application Ser. No. 07/670,496, filed Mar. 15, 1991 (now abandoned), which is a continuation of application Ser. No. 07/194,824, filed May 17, 1988 (now abandoned).

FIELD OF THE INVENTION

The invention is in the area of plant molecular biology and concerns plant genetic engineering by recombinant DNA technology. The identification and characterization of a segment of DNA from the upstream nontranscribed region of a plant ubiquitin gene are described. This segment is capable of initiating and driving the transcription of nearby plant expressible genes in recombinant DNA-containing tissue from both monocotyledonous and dicotyledonous plants. The described DNA segment will enable the selective expression and regulation of desired structural genes in plant tissue.

BACKGROUND OF THE INVENTION

Ubiquitin is an 8.5 kDa protein found in eukaryotic cells in either the free, monomeric state or covalently joined to various cytoplasmic, nuclear or membrane proteins. This protein contains 76 amino acid residues and its amino acid sequence is conserved to an unusually high extent. The sequence of ubiquitin is identical between species as diverse as human, cow, Mediterranean fruit fly, Xenopus and chicken (U. Bond and M. Schlesinger (1985) Mol. Cell. Biol. 5:949–956). Yeast and human ubiquitin differ by only three different amino acids (K. Ozkaynak et al. (1984) Nature 312:663–666), while plant ubiquitin differs from that of yeast by two amino acids. Based on this two or three amino acid difference in sequence, there appear to be at least 3 types of ubiquitin—animal, plant and yeast.

Ubiquitin is found in three major cellular compartments—the cytoplasmic membrane, the cytoplasm and the nucleus. This protein is required for ATP—dependent degradation of intracellular proteins, a non-lysosomal pathway to eliminate from the cell those proteins that are damaged or abnormal as well as normal proteins having a short half-life (A. Hershko et al. (1984) Proc. Natl. Acad. Sci. USA 81:1619–1623; D. Finley et al. (1985) Trends Biol. Sci. 10:343–347). Ubiquitin binds to a target protein, tagging it for degradation. The covalent attachment is through isopeptide linkages between the carboxyl-terminus (glycine) in ubiquitin and the $\epsilon$-amino group of lysyl side chains in the target proteins.

Ubiquitin also plays a role in the cellular response to stresses, such as heat shock and increase in metal (arsenite) concentration (D. Finley et al. (1985) supra). Most living cells respond to stress (for example, exposure to temperatures a few degrees above normal physiological temperatures or to elevated concentrations of heavy metals, ethanol, oxidants and amino acid analogs) by activating a small set of genes to selectively synthesize stress proteins, also called heat shock proteins. In most organisms these stress proteins were found to have subunit molecular weights of 89, 70 and 24 kDa (U. Bond and M. Schlesinger (1985) supra). Ubiquitin, with a molecular weight of approximately 8.5 kDa, also responds to stress, since in different species (yeast, mouse, gerbil and chicken embryo fibroblasts) the levels of ubiquitin mRNA and ubiquitin protein increase as a result of different stress conditions.

In eukaryotic systems the expression of genes is directed by a region of the DNA sequence called the promoter. In general, the promoter is considered to be that portion of the DNA, upstream from the coding region, that contains the binding site for RNA polymerase II and initiates transcription of the DNA. The promoter region also comprises other elements that act as regulators of gene expression. These include a TATA box consensus sequence in the vicinity of about −30, and often a CAAT box consensus sequence at about −75 bp 5' relative to the transcription start site, or cap site, which is defined as +1 (R. Breathnach and P. Chambon (1981) Ann. Rev. Biochem. 50:349–383; J. Messing et al. (1983) in *Genetic Engineering of Plants*, eds. T. Kosuge, C. P. Meredith and A. Hollaender, pp. 211–227). In plants the CAAT box may be substituted by the AGGA box (J. Messing et al. (1983) supra). Other regulatory elements that may be present are those that affect gene expression in response to environmental stimuli, such as illumination or nutrient availability, or to adverse conditions, such as heat shock, anaerobiosis or the presence of heavy metal. In addition, there may be present DNA sequences which control gene expression during development, or in a tissue-specific fashion. Other regulatory elements that have been found are the enhancers (in animal systems) or the upstream activating sequences (in yeast), that act to elevate the overall expression of nearby genes in a manner that is independent of position and orientation with respect to the nearby gene. Sequences homologous to the animal enhancer core consensus sequence, 5'-GGTGTGGAAA(orTTT)G-3', have been described in plants, for example, in the pea legumin gene at about position −180 relative to the transcription start site (G. Lycett et al. (1984) Nucleic Acids Res. 12:4493–4506) and in the maize Adh1 and Adh2 genes at about −200 and −170 bp, respectively, from the transcription start site. In general, promoters are found 5', or upstream, relative to the start of the coding region of the corresponding gene and this promoter region, comprising all the ancillary regulatory elements, may contain between 100 and 1000 or more nucleotides.

Of the regulatory elements controlling gene expression, the heat shock element is perhaps one of the most widely studied. Although the universality of cellular response to heat shock has been known for almost a decade, very little is known yet about the function of the heat shock proteins selectively synthesized by the stressed cell. The induction of stress protein synthesis occurs at a transcriptional level and the response has been found to be similar in bacteria, fungi, insects and mammals (E. Craig (1985) CRC Crit. Rev. Biochem. 18:239–280). In addition to the synthesis and accumulation of the classic heat shock proteins in response to stress, cells that are stressed also synthesize proteases and ubiquitin. In *E. coli*, a 94 kDa enzyme that has an ATP-dependent proteolytic activity is encoded by the lon (cap R) gene whose expression is under control of the heat shock regulon (E. Ozkaynak et al. (1984) Nature 312:66–666). In chicken embryo fibroblasts (U. Bond and M. Schlesinger (1985) Mol. Cell. Biol. 5:949–956) the ubiquitin mRNA level increased five fold after heat shock or after exposure to 50 $\mu$M arsenite. Each mRNA comprises sequences encoding tandemly repeated identical polypeptides which, upon translation as a polyubiquitin molecule, gives rise to multiple ubiquitin molecules, offering a distinctive mechanism for amplifying genetic information. This elevated level of ubiquitin mRNA does not persist during the recovery phase after heat shock, indicating a transient role for free ubiquitin during the stress response.

It has been postulated (J. Ananthan et al. (1986) Science 232:522–524) that metabolic stresses that trigger the activation of heat shock protein genes act through a common mechanism. The metabolic stresses that activate heat shock genes cause denaturation of intracellular proteins; the accumulation of abnormal proteins acts as a signal to activate heat shock genes. A role for ubiquitin in targeting abnormal proteins for degradation, as well as for different proteolytic enzymes, would be compatible with such a model of heat shock protein gene regulation.

Most of the early work on heat shock genes was done with Drosophila species. In particular, the Drosophila hsp70 gene was used widely in recombinant studies. In homologous systems, the Drosophila hsp70 gene was fused to the E. coli β-galactosidase structural gene to allow the activity of the hybrid gene to be distinguished from the five resident hsp70 heat shock genes in the recipient Drosophila. Drosophila heat shock genes were also introduced into heterologous systems, e.g., in monkey COS cells and mouse cells (H. Pelham (1982) Cell 30:517–528). Regulation by heat shock was observed in the hybrid hsp70-lac Z gene which was integrated into the Drosophila germ line and into which a 7 kb E. coli β-galactosidase DNA fragment was inserted into the middle of the hsp70 structural gene. The resultant β-galactosidase activity in the transformants was shown (J. Lis et al. (1983) Cell 35:403–410) to be regulated by heat shock.

The DNA sequence conferring heat shock response was identified by deletion analysis of the Drosophila hsp70 heat shock promoter to 5'-CTGGAATNTTCTAGA-3' (where N=A, T, C, or G) (H. Pelham et al. (1982) in *Heat Shock From Bacteria to Man*, Cold Spring Harbor Laboratory, pp. 43–48) and is generally located in the −66 through −47 region of the gene or approximately 26 bases upstream of the TATA box. It was further demonstrated that a chemically synthesized copy of this element, when placed upstream of the TATA box of the herpes virus thymidine kinase gene in place of the normal upstream promoter element, was sufficient to confer heat inducibility upon the thymidine kinase gene in monkey COS cells and in Xenopus oocytes. (The thymidine kinase gene is normally not heat inducible.) These heat shock sequences interact with heat shock specific transcription factor(s) which allow the induction of heat shock proteins (C. Parker et al. (1984) Cell 37:273–283). Inducers of heat shock genes could be factors that alter (decrease) the concentration of heat shock proteins within the cell and, thus, control the transcription and translation of heat shock genes.

In higher plants, the stress response was demonstrated by increased protein synthesis in response to heat shock in soybean, pea, millet, corn, sunflower, cotton and wheat (T. Barnett et al. (1980) Dev. Genet. 1:331–340; J. Key et al. (1981) Proc. Nat. Acad. Sci. USA 78:3526–3530). The major differences in heat shock response seen among plant species are: (a) the amount of total protein synthesized in response to stress, (b) the size (1981)-(1981).distribution of the different proteins synthesized, (c) the optimum temperature of induction of heat shock proteins and (d) the lethal (breakpoint) temperature. High molecular weight proteins are found to be electrophoretically similar among different species. The low molecular weight (15–27 kDa) heat shock proteins show more electrophoretic heterogeneity between species. In plants, the higher molecular weight proteins resemble those produced in Drosophila. There is a marked difference, however, in the complexity of the low molecular weight heat shock proteins between plants and Drosophila. Four heat shock proteins, 22,23,26 and 27 kDa, are synthesized in Drosophila, whereas soybean produces over 20 heat shock proteins having molecular weights in the range of 15–18 kDa. The low molecular weight protein genes in soybeans are the most actively expressed and coordinately regulated genes under heat shock conditions (F. Schoffl et al. (1982) J. Mol. Appl. Genet. 1:301–314).

Key et al. (U.S. patent application Ser. No. 599,993, filed Apr. 13, 1984) have studied the promoter region of plant heat shock genes. Four soybean heat shock genes (three genes coding for 15–18 kDa heat shock proteins and one gene coding for a 17.3 kDa heat shock protein) were cloned and sequenced. The coding sequences and flanking sequences of the four heat shock genes were determined. The promoter regions of these four genes were subcloned, linked to a T-DNA shuttle vector and transferred into *Agrobacterium tumefaciens*. One of the recombinant clones of a soybean heat shock gene coding for a 15–18 kDa protein contained an open reading frame of 462 nucleotides and a 291 nucleotide promoter region upstream of the ATG translation initiation codon. The promoter included the TATA box, the CAAT box, the transcription initiation site and a heat shock consensus sequence 131–144 nucleotides upstream of the ATG translation start codon with the sequence 5'-CTNGAANNTTCNAG-3' (where N=A, T,C, or G). Only three of the four clones showed substantial homology in the promoter region, but there were strong similarities between the heat shock consensus; sequences of all four clones. Significantly, the coding sequence, the upstream promoter region and the downstream flanking region of the four soybean heat shock genes had almost no resemblance to the corresponding regions of Drosophila heat shock genes. Although there were similarities between the consensus sequence of the promoter region from Drosophila and soybean heat shock genes, the promoter regions of soybean heat shock genes did not possess the inverted repeat sequences characteristic of Drosophila genes.

The promoter region from the soybean heat shock genes was used to activate a soybean gene and a foreign gene (one normally not found in soybean) and to show regulation of the response by stress (Key et al. U.S. patent application Ser. No. 599,993, filed Apr. 13, 1984). The promoter was isolated from the soybean SB 13 heat shock gene as a DNA fragment extending 65 bp downstream from the start of transcription to include a major portion of the untranslated leader sequence but not the start codon for translation. A β-galactosidase gene was placed under the control of the heat shock promoter within the T-DNA of the Ti-plasmid in a stable form within *A. tumefaciens* and then was transferred to a plant or plant cell culture. The actuality of DNA transfer was recognized by the expression of the β-galactosidase gene as the production of a blue color after heat treatment in a medium containing the 5-bromo-4-chloro-3-indolyl-β-D-galactoside substrate molecule (M. Rose et al. (1981) Proc. Natl. Acad. Sci. USA 78:2460–2464).

Experimentation with cross expression wherein a gene from one plant species is examined for expression in a different species adds a further dimension to the understanding of specific function. These experiments may embody the insertion of a gene under the control of its own promoter or of a gene artificially fused to a different or unnatural promoter. In 1983 Murai et al. (Science 222:476–482)

obtained expression of the phaseolin gene from *Phaseolus vulgaris* L. in sunflower (Helianthus) tissue under two sets of conditions: (i) when the Phaseolin gene was under the control of its own promoter and (ii) when the gene was spliced to, and under the control of a T-DNA promoter. In subsequent experiments it was shown that the phaseolin structural gene under the control of its natural promoter could be expressed in tobacco and that the tissue-specific expression in the heterologous host (tobacco) was similar to that in the native host (bean) (C. Sengupta-Gopalan et al. (1985) Proc. Natl. Acad. Sci. USA 82:3320–3324).

In later experiments (J. Jones et al. (1985) EMBO J. 4:2411–2418) the expression of the octopine synthetase gene (ocs) was described in both regenerated transformed homologous (petunia) and heterologous (tobacco) plants. In this study the ocs gene was fused to the promoter of a petunia chlorophyll a/b binding protein. Cross-expression was also obtained by W. Gurley et al. (1986) (Mol. Cell. Biol. 6:559–565) and Key et al. (U.S. Patent application Ser. No. 599,993, filed Apr. 13, 1984), who reported strong transcription in sunflower tumor tissue of a soybean heat shock gene under control of its own promoter. In this case functional activity was measured as the correct thermal induction response.

The first evidence for transcription initiated from a monocotyledon promoter in a dicotyledon host plant was published by Matzke et al. (1984) (EMBO J. 3:1525–1531). These workers cloned the maize zein Z4 gene and introduced it on a Ti-derived vector into sunflower stemlets. The ensuing zein (1981)mRNA could then be translated in a wheat germ system but not in the transformed sunflower calli.

In a later study the wheat gene whAB1.6 encoding the major chlorophyll a/b binding protein was cloned into a T-DNA-containing vector and transferred to both petunia and tobacco (G. Lamppa et al. (1985) Nature 316:750–752). Expression was obtained in the and dicotyledon hosts and was determined to be light-induced and tissue-specific. In a more recent study, Rochester et al. (1986) (EMBO J. 5:451–458) obtained expression of the maize heat shock hsp70 gene in transgenic petunia. The maize hsp70 mRNA was synthesized only in response to thermal stress. So far, these three studies constitute the total number of published reports describing successful expression of monocot genes in transgenic dicot plants. However, there are also negative reports describing minimal or no expression of maize alcohol dehydrogenase genes in tobacco hosts (Llewellyn et al. (1985) in *Molecular Form and Function of the Plant Genome*, L. van Vloten-Doting, G. S. Groot and T. Hall (eds), Plenum Publishing Corp., pp 593–608; J. G. Ellis et al. (1987) Embo J. 6:11–16), suggesting a possible inherent species-specific difference between monocot and dicot promoters.

The heat shock response is believed to provide thermal protection or thermotolerance to otherwise nonpermissive temperatures (M. Schlesinger et al. (1982) in *Heat Shock from Bacteria to Man*, Cold Spring Harbor Laboratory, Cold Spring Harbor, N.Y., p. 329). A permissive heat shock temperature is a temperature which is high enough to induce the heat shock response but not high enough to be lethal.

Thermotolerance in plant seedlings can be attained by different treatment regimes: (a) a 1 to 2 hour exposure to continuous heat shock at 40° C. followed by a 45° C. incubation, (b) a 30 min heat shock at 40° C. followed by 2 to 3 hours at 28° C. prior to the shift to 45° C., (c) a 10 min heat shock at 45° C. followed by about 2 hours at 28° C. prior to the shift to 45° C. and (d) treatment of seedlings with 50 μM arsenite at 28° C. for 3 hours or more prior to the shift to 45° C. During the pretreatment prior to incubation at the potentially lethal temperature, heat shock proteins are synthesized and accumulated. Also, heat shock mRNA and protein synthesis occur at 45° C., if the plant seedling is preconditioned as described above. When the temperature is shifted back to physiological levels (e.g., 28° C.), normal transcription and translation are resumed and after 3 to 4 hours at normal temperature, there is no longer detectable synthesis of heat shock proteins (J. Key et al. (1981) Proc. Natl. Acad. Sci. USA 78:3526–3530; M. Schlesinger et al. (1982) Trends Biochem. Sci. 1:222–225). The heat shock proteins that were synthesized during the 40° C. heat shock treatment are very stable and are not immediately degraded.

Although ubiquitin is regulated in response to environmental stress, including heat shock, the regulation of ubiquitin transcription differs from that of classical heat shock protein transcripts. Both ubiquitin and heat shock protein mRNA levels are elevated in response to cellular stress. However, whereas classical heat shock proteins accumulate during heat shock and persist during the recovery phase, ubiquitin mRNAs accumulated during heat shock are rapidly degraded within hours after stress treatment. This unstable mRNA transcript suggests a specialized but transient role for ubiquitin during heat shock, and implicates a unique DNA sequence in the ubiquitin gene promoter region, specifying specialized regulatory control during cellular response to stress.

SUMMARY OF THE INVENTION

The primary object of this invention is to provide novel DNA segments and constructions comprising a regulatory promoter system which will enable those skilled in the art to express selectively structural genes in plant tissue. The promoter comprises the DNA sequences from the 5° non-transcribed regions of plant ubiquitin genes that initiate and regulate the transcription of genes placed under its control. In its preferred embodiment, the promoter sequence is derived from the upstream region of the ubiquitin gene from maize.

The isolation and characterization of a promoter system which is active in plants to control and regulate the expression of a downstream gene is described in the present work. This DNA sequence is found as a naturally occurring region upstream of the ubiquitin structural gene isolated from a maize genomic library. The transcription start site or cap site as determined by S1 nuclease mapping is designated as base 1 and the sequences embodied within about 899 bases 5° of the transcription start site plus about 1093 bases 3° of the cap site but 5° of the translation start site constitute the ubiquitin promoter. Located within this approximately 2 kb promoter region are a TATA box (−30), two overlapping heat shock consensus elements (−204 and −214), an 83 nucleotide leader sequence immediately adjacent to the transcription start site and an intron extending from base 84 to base 1093.

A further object of this invention is to provide a recombinant DNA molecule comprising a plant expressible promoter and a plant expressible structural gene, wherein the structural gene is placed under the regulatory control of all transcription initiating and activating elements of the promoter. In particular, the plant ubiquitin promoter can be combined with a variety of DNA sequences, typically structural genes, to provide DNA constructions for regulated transcription and translation of said DNA sequences and which will allow for regulated control of expression when stressed with elevated temperatures.

Such recombinant DNA molecules are introduced into plant tissue so that the promoter/structural gene combination is expressed. It is contemplated that the method of the present invention is generally applicable to the expression of structural genes in both monocotyledonous and dicotyledonous plants.

BRIEF DESCRIPTION OF THE FIGURES

FIG. 2 documents the DNA sequence and the deduced amino acid sequence of ubiquitin gene 1. The start of transcription as determined by S1 nuclease mapping is denoted as base 1. Sequences representing the putative "TATA" box (−30) and the overlapping heat shock consensus sequences (−214 and −204) are underlined. The intron extends from base 84 to base 1093 and the polyubiquitin protein coding sequence extends from base 1094 to 2693.

BRIEF DESCRIPTION OF THE SEQUENCES

Figure 1:
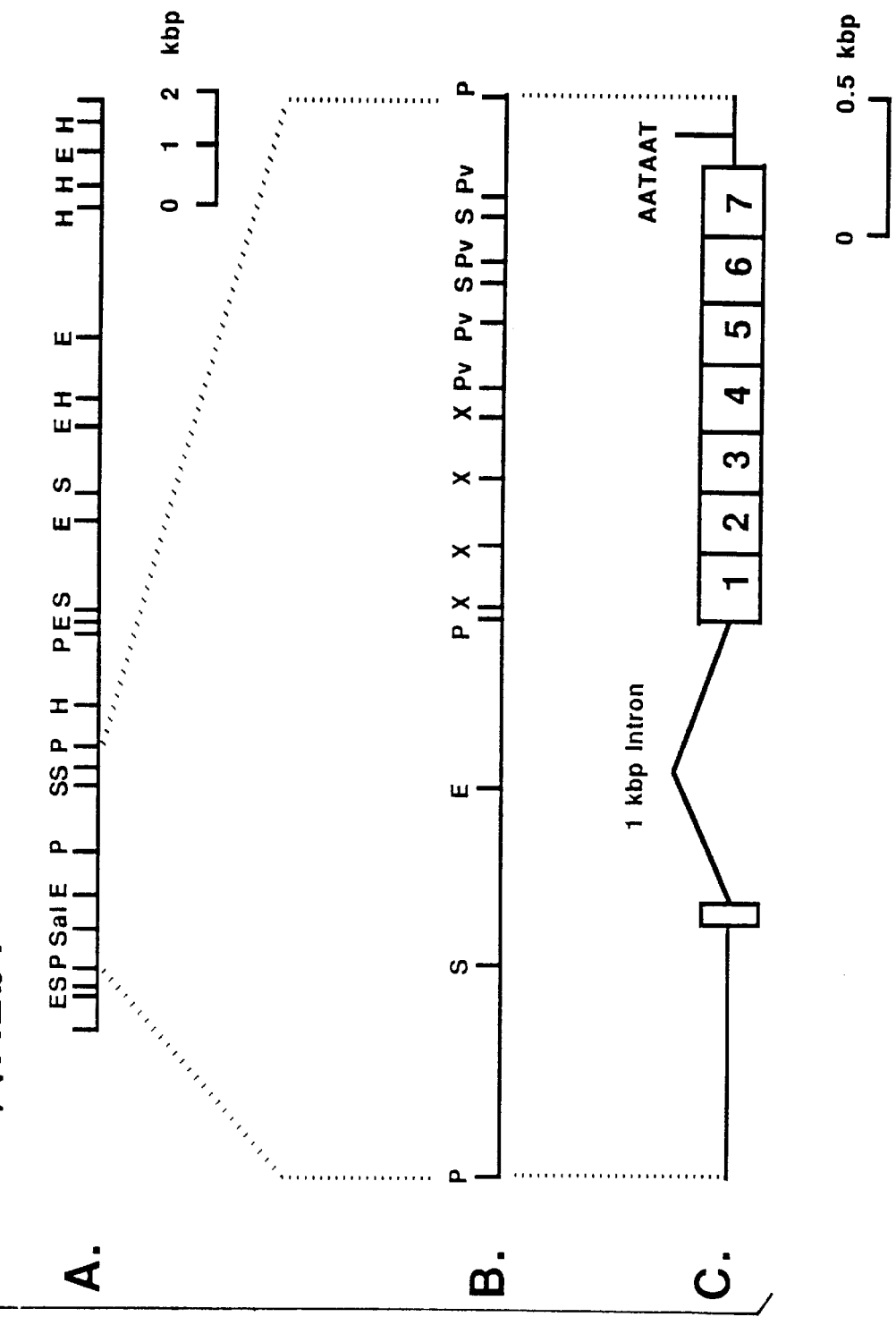
FIG. 1 is an analysis of a maize ubiquitin genomic clone. (A) Restriction map of ubiquitin gene 1, lambda 7.2b1. (B) Restriction map of two subcloned Pst1 fragments of ubiquitin gene 1. (C) Schematic representation of maize ubiquitin gene 1 organization. The 5' untranslated exon is indicated by the open box and the tandem ubiquitin coding regions are indicated by the numbered boxes E, EcoRI;S, SacI,P,PstI;SAI,SAlI,H,HindIII;X,XhoI;PV, PvuII.

SEQ ID NO. 1 is the nucleotide sequence of ubiquitin gene 1.

SEQ ID NO. 2 is the deduced amino acid sequence encoded by ubiquitin gene 1.

DETAILED DESCRIPTION OF THE INVENTION

The following definitions are provided in order to remove ambiguities as to the intent or scope of their usage in the specification and claims.

Expression refers to the transcription and/or translation of a structural gene.

Promoter refers to the nucleotide sequences at the 5' end of a structural gene which direct the initiation of transcription. Promoter sequences are necessary, but not always sufficient, to drive the expression of a downstream gene. In general, eukaryotic promoters include a characteristic DNA sequence homologous to the consensus 5'-TATAAT-3' (TATA) box about 10–30 bp 5' to the transcription start (cap) site, which, by convention, is numbered +1. Bases 3' to the cap site are given positive numbers, whereas bases 5' to the cap site receive negative numbers, reflecting their distance from the cap site. Another promoter component, the CAAT box, is often found about 30 to 70 bp 5' to the TATA box and has homology to the canonical form 5'-CCAAT-3' (R. Breathnach and P. Chambon (1981) Ann. Rev. Biochem. 50:349–383). In plants the CAAT box is sometimes replaced by a sequence known as the AGGA box, a region having adenine residues symmetrically flanking the triplet G(orT)NG (J. Messing et al. (1983), in *Genetic Engineering of Plants*, T. Kosuge, C. Meredith and A. Hollaender (eds.), Plenum Press, pp. 211–227). Other sequences conferring regulatory influences on transcription can be found within the promoter region and extending as far as 1000 bp or more 5' from the cap site.

Regulatory Control refers to the modulation of gene expression induced by DNA sequence elements located primarily, but not exclusively, upstream of (5' to) the (1981)-(1981)- transcription start site. Regulation may result in an all-or-nothing response to environmental stimuli, or it may result in variations in the level of gene expression. In this invention, the heat shock regulatory elements function to enhance transiently the level of downstream gene expression in response to sudden temperature elevation.

Placing a structural gene under the regulatory control of a promoter or a regulatory element means positioning the structural gene such that the expression of the gene is controlled by these sequences. In general, promoters are found positioned 5' (upstream) to the genes that they control. Thus, in the construction of heterologous promoter/structural gene combinations, the promoter is preferably positioned upstream to the gene and at a distance from the transcription start site that approximates the distance between the promoter and the gene it controls in its natural setting. As is known in the art, some variation in this distance can be tolerated without loss of promoter function. Similarly, the preferred positioning of a regulatory element with respect to a heterologous gene placed under its control reflects its natural position relative to the structural gene it naturally regulates. Again, as is known in the art, some (1981). variation in this distance can be accommodated.

Promoter function during expression of a structural gene under its regulatory control can be tested at the transcriptional stage using DNA-RNA hybridization assays ("Northern" blots) and at the translational stage using specific functional assays for the protein synthesized (for example, by enzymatic activity or by immunoassay of the protein).

Structural gene is that portion of a gene comprising a DNA segment encoding a protein, polypeptide or a portion thereof, and excluding the 5' sequence which drives the initiation of transcription. The structural gene may be one which is normally found in the cell or one which is not normally found in the cellular location wherein it is introduced, in which case it is termed a heterologous gene. A heterologous gene may be derived in whole or in part from any source known to the art, including a bacterial genome or episome, eukaryotic, nuclear or plasmid DNA, cDNA, viral DNA or chemically synthesized DNA. A structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bound by the appropriate splice junctions. The structural gene may be a composite of segments derived from a plurality of sources, naturally occurring or synthetic. The structural gene may also encode a fusion protein. It is contemplated that the introduction into plant tissue of recombinant DNA molecules containing the promoter/structural gene/polyadenylation signal complex will include constructions wherein the structural gene and its promoter are each derived from different plant species.

Plant Ubiquitin Regulatory System refers to the approximately 2 kb nucleotide sequence 5' to the translation start site of the maize ubiquitin gene and comprises sequences that direct initiation of transcription, regulation of transcription, control of expression level, induction of stress genes and enhancement of expression in response to stress. The regulatory system, comprising both promoter and regulatory functions, is the DNA sequence providing regulatory control or modulation of gene expression. A structural gene placed under the regulatory control of the plant ubiquitin regulatory system means that a structural gene is positioned such that the regulated expression of the gene is controlled by the sequences comprising the ubiquitin regulatory system.

Polyadenylation signal refers to any nucleic acid sequence capable of effecting mRNA processing, usually characterized by the addition of polyadenylic acid tracts to the 3'-ends of the mRNA precursors. The polyadenylation signal DNA segment may itself be a composite of segments derived from several sources, naturally occurring or synthetic, and may be from a genomic DNA or an mRNA-derived cDNA. Polyadenylation signals are commonly recognized by the presence of homology to the canonical form 5' -AATAA-3', although variation of distance, partial "readthrough", and multiple tandem canonical sequences are not uncommon (J. Messing et al. supra). It should be recognized that: a canonical "polyadenylation signal" may in fact cause transcriptional termination and not polyadenylation per se (C. Montell et al. (1983) Nature 305:600–605).

Plant tissue includes differentiated and undifferentiated tissues of plants, including, but not limited to roots, shoots, leaves, pollen, seeds, tumor tissue and various forms of cells in culture, such as single cells, protoplasts, embryos and callus tissue. The plant tissue may be in planta or in organ, tissue or cell culture.

Homology, as used herein, refers to identity or near identity of nucleotide and/or amino acid sequences. As is understood in the art, nucleotide mismatches can occur at the third or wobble base in the codon without causing amino acid substitutions in the final polypeptide sequence. Also, minor nucleotide modifications (e.g., substitutions, insertions or deletions) in certain regions of the gene sequence can be tolerated and considered insignificant whenever such modifications result in changes in amino acid sequence that do not alter the functionality of the final product. It has been shown that chemically synthesized copies of whole, or parts of, gene sequences can replace the corresponding regions in the natural gene without loss of gene function. Homologs of specific DNA sequences may be identified by those skilled in the art using the test of cross-hybridization of nucleic acids under conditions of stringency as is well understood in the art (as described in Hames and Higgins (eds.) (1985) Nucleic Acid Hybridization, IRL Press, Oxford, UK). Extent of homology is often measured in terms of percentage of identity between the sequences compared. Thus, in this disclosure it will be understood that minor sequence variation can exist within homologous sequences.

Derived from is used herein to mean taken, obtained, received, traced, replicated or descended from a source (chemical and/or biological). A derivative may be produced by chemical or biological manipulation (including but not limited to substitution, addition, insertion, deletion, extraction, isolation, mutation and replication) of the original source.

Chemically synthesized, as related to a sequence of DNA, means that the component nucleotides were assembled in vitro. Manual chemical synthesis of DNA may be accomplished using well established procedures (M. Caruthers (1983) in Methodoloqy of DNA and RNA Sequencing, Weissman (ed.), Praeger Publishers (New York) Chapter 1), or automated chemical synthesis can be performed using one of a number of commercially available machines.

Heat shock elements refer to DNA sequences that regulate gene expression in response to the stress of sudden temperature elevations. The response is seen as an immediate albeit transitory enhancement in level of expression of a downstream gene. The original work on heat shock genes was done with Drosophila but many other species including plants (T. Barnett et al. (1980) Dev. Genet. 1:331–340) exhibited analogous responses to stress. The essential primary component of the heat shock element was described in Drosophila to have the consensus sequence 5'-CTGGAATNTTCTAGE-3' (where N=A, T, C, or G) (Support for this definition of N is found in the Messing et al. reference) and to be located in the region between residues −66 through −47 bp upstream to the transcriptional start site (H. Pelham et al. (1982) supra). A chemically synthesized oligonucleotide copy of this consensus sequence can replace the natural sequence in conferring heat shock inducibility. In other systems, multiple heat shock elements were identified within the promoter region. For example, Rochester et al. (1986) supra recognized two heat shock elements in the maize hsp 70 gene.

Leader sequence refers to a DNA sequence comprising about 100 nucleotides located between the transcription start site and the translation start site. Embodied within the leader sequence is a region that specifies the ribosome binding site.

Introns or intervening sequences refer in this work to those regions of DNA sequence that are transcribed along with the coding sequences (exons) but are then removed in the formation of the mature mRNA. Introns may occur anywhere within a transcribed sequence—between coding sequences of the same or different genes, within the coding sequence of a gene, interrupting and splitting its amino acid sequences, and within the promoter region (5' to the translation start site). Introns in the primary transcript are excised and the coding sequences are simultaneously and precisely ligated to form the mature mRNA. The junctions of introns and exons form the splice sites. The base sequence of an intron begins with GU and ends with AG. The same splicing signal is found in many higher eukaryotes.

The present invention relates to the development of a recombinant vector useful for the expression of DNA coding segments in plant cells. The vector herein described employs a maize ubiquitin promoter to control expression of an inserted DNA coding segment. The transcriptional regulatory sequences may be combined with an extrachromosomal replication system for a predetermined host. Other DNA sequences having restriction sites for gene insertion may be added to provide a vector for the regulated transcription and translation of the inserted genes in said host. The vector may also include a prokaryotic replication system allowing amplification in a prokaryotic host, markers for selection and other DNA regions. This would allow large quantities of the vector to be grown in well characterized bacterial systems prior to transforming a plant or mammalian host. The principles for construction of a vector having proper orientation of the promoter and coding sequences with respect to each other are matters well-known to those skilled in the art. In some situations it may be desirable to join the promoter system to a desired structural gene and to introduce the resultant construct DNA directly into a host. Methods for such direct transfers include, but are not limited to, protoplast transformation, electroporation, direct injection of DNA into nuclei and co-transformation by calcium precipitation.

This invention comprises the first report of an isolated and characterized plant ubiquitin promoter. The maize ubiquitin promoter system as described in the present work includes the RNA polymerase recognition and binding sites, the transcriptional initiation sequence, regulatory sequences responsible for inducible transcription and an untranslatable intervening sequence (intron) between the transcriptional start site and the translational initiation site. Two overlapping heat shock consensus promoter sequences are situated 5' (−214 and −204) of the transcriptional start site. An exon of 83 nucleotides is located immediately adjacent to the cap site and is followed by a large (approximately 1 kb) intron.

The ubiquitin promoter system along with the ubiquitin structural gene can be isolated on two approximately 2 kb Pst1 fragments of the maize genome (FIG. 1). The entire fragment can be used to show promoter function by monitoring expression of mRNA or protein. Introduction of a heterologous gene downstream of the ubiquitin translation initiation codon will result in the expression of a fused protein. Insertion of a heterologous gene (having its own start and stop codons) between the ubiquitin promoter and translation initiation codon will result in the expression of the native polypeptide corresponding to the inserted gene. The insertion of the desired structural gene is most conveniently accomplished with the use of blunt-ended linkers at the ends of the gene.

Alternatively, the ubiquitin gene fragment may be restricted, particularly at a site immediately preceding the start of the structural gene or at a site preceding the transcription start site. For example, in the present invention the promoter fragment was derived from the ubiquitin gene as an approximately 2 kb Pst1 fragment. To ensure that the promoter fragment is devoid of the translational initiation codon, the fragment containing the 5' flanking region may be selectively digested with double stranded exonuclease under controlled conditions to remove a desired number of nucleotide pairs. It is desirable to remove the ubiquitin translation initiation codon so that translation of the inserted gene will commence at its own start site. The isolated (and shortened) promoter fragment may then be inserted into the vector using linkers or homopolymer tailing to introduce desired restriction sites compatible with the remaining regions of the vector. In general, the promoter fragment may be cleaved with specific restriction enzymes and the resultant shortened DNA fragments tested for promoter function and compared to that of the intact promoter. In addition, DNA codons may be added and/or existing sequences may be modified to give derivative DNA fragments retaining promoter functions.

The resulting DNA constructs may be useful as cloning vehicles for a structural gene of interest in a plant host. In this invention, the structural gene encoding CAT under control of either the maize ubiquitin promoter or the cauliflower mosaic virus promoter was expressed in both oat and tobacco cells. When the ubiquitin promoter was employed, a greater degree of expression was obtained with the monocot host than with the dicot host; however, a higher level of expression was obtained with dicot than with monocot host when the cauliflower mosaic virus promoter was utilized. The differential in expression levels reflects the inherent inequality of different promoters as well as basic cellular differences in regulation of expression and processing between monocots and dicots. To date, it is not predictable, routine or obvious that a monocot promoter will operate in a dicot host cell.

A wide variety of structural genes may be introduced into the subject DNA cloning vectors for the production of desired proteins, such as enzymes, hormones and the like. In addition, DNA constructs of this type can be used for the enhanced production of DNA derived from a particular gene, as well as for enhanced production of mRNA which can be used to produce cDNA. Such vectors carrying specific DNA sequences find wide application and are quite versatile; for example, they can be used for amplification in bacteria as well as for expression in higher cells which allow for additional cellular functions. An advantage of utilizing higher eukaryotic recombinant systems to produce commercially medical and agriculturally desirable proteins is that they ensure correct post-translational modifications which may otherwise be difficult to duplicate in prokaryotic and lower eukaryotic hosts.

In this invention the maize ubiquitin promoter system was shown to function in oat and tobacco, as examples of monocots and dicots, respectively, and it is conceivable that this promoter can function in yet other cells. Such systems include, by way of example, and without limitation, other cells from which ubiquitin genes have been isolated and found to be highly conserved, for example, other monocots in addition to maize, dicots other than tobacco, lower eukaryotic organisms such as yeast and mammalian cells. The screening of cellular systems suitable for use with the maize ubiquitin promoter can be accomplished according to the teaching herein, without undue experimentation. The construction of vectors suitable for the expression of a DNA coding segment in individual systems has been well documented. Shuttle vectors capable of replication in more than one host have also been described, for example, shuttle expression vectors for both yeast and mammalian cells, for plants and animal cells and for plants and bacterial cells. In addition, it will be understood that ubiquitin genes from any other system, that are similar to the maize ubiquitin gene in functioning as a plant promoter, may be employed as the source for the ubiquitin promoter sequence.

The present invention also relates to the utilization of the maize ubiquitin promoter system as a heat shock promoter. Two heat shock consensus sequences are located upstream of the maize ubiquitin gene at positions −214 and −204. In many eukaryotes, naturally occurring and chemically-synthesized sequences homologous to the heat shock consensus sequence have been shown to regulate the induction of gene expression. Although the ubiquitin promoter system contains sequences that are identified as being those of heat shock elements, the promoter is distinguished from classical heat shock promoters (1) in having a nontranslated intron 3' to the transcription start site and (2) in regulating ubiquitin expression constitutively as well as inductively. The functional relationship between heat shock elements and the presence of a large intron within the promoter region is unknown to prior art. The nucleotide distance between these characteristic features and also the directionality and orientation of one element with respect to the other are presumed in the present work to be variable, as long as the basic promoter function of the derivative regulatory fragments remains active.

The presence of an intron in the promoter system has been related to the relative stability of the unprocessed mRNA transcript and, indirectly, to the level of protein synthesized (Callis et al. (1987) Genes and Development 1:1183–1200). Constitutively expressed ubiquitin mRNA has been reported to be maintained at stable levels in chicken embryo fibroblasts, whereas ubiquitin mRNA formed in response to stress has a half-life of approximately 1.5 to 2 h.

In yeast four distinct ubiquitin-coding loci have been described. Constitutively expressed ubiquitin is encoded by one or more of three of the ubiquitin genes, two of which contain an approximately 400 bp intron immediately within the coding region. The fourth ubiquitin gene, devoid of a nontranslated intron but comprising multiple heat shock elements, functions primarily in inducing ubiquitin expression in response to stress. It has been shown that the latter ubiquitin gene does not act constitutively but rather is turned on in response to heat shock or stress signal (E. Ozkaynak et al. (1987) EMBO J. 6:1429–1439).

In maize, ubiquitin is encoded by a small multigene family. In this invention is presented the nucleotide sequence of one of the ubiquitin genes. A large (approximately 1 kb) intron between the transcriptional and the translational start sites as well as nucleotide sequences corresponding to consensus heat shock sequences are found within the maize ubiquitin promoter system. These two regions of specialization most probably are involved in ubiquitin synthesis and in regulating the ubiquitin level in response to external influences. The functional relationship between the intron and the heat shock elements encompassed within the ubiquitin promoter system is unknown. It is reported in this invention that the maize ubiquitin promoter system regulates the synthesis of mRNA both under normal and under heat shock conditions and that changes in the regulation of transcription account for the enhancement in ubiquitin synthesis after heat shock.

The following examples are offered by way of illustration and not by way of limitation.

EXAMPLES

Example 1

Isolation and Characterization of the Maize Ubiquitin Gene

A. Growth of Plants

Zea mays Inbred line B73 was grown in moist vermiculite for 4 to 5 days at 25° C. in the dark. The portion of the seedlings from the mesocotyl node to the shoot tip was harvested, frozen in liquid nitrogen and stored at −80° C.

B. RNA Isolation and Analysis

Total cellular RNA was extracted from frozen tissue using the guanidine thiocyanate procedure. Poly(A)+RNA was isolated from total cellular RNA by passage over a poly U-Sephadex (Bethesda Research Laboratories, Gaithersburg, Md.) column. Total or poly(A)+RNA was electrophoresed in 1.5% agarose gels containing 3% (wt/vol) formaldehyde. RNA was transferred to Gene Screen™ (DuPont) by capillary blotting using 25 mM sodium phosphate (pH6.5).

Blots were prehybridized in 50% formamide, 5XSSC, 100 µg denatured salmon DNA, 40 mM sodium phosphate (pH6.8), 0.5% BSA and 1% SDS. Blots were hybridized in 50% formamide, 5XSSC, 100 µg/ml denatured salmon DNA, 40 mM sodium phosphate (pH6.8) and 10% dextran sulfate.

C. cDNA Library Construction

Double stranded CDNA was synthesized from poly(A)+ RNA by a modification of the method of Murray et al. (1983) Plant Mol. Biol. 2:75–84. Oligo(dC)-tailing of the double-stranded CDNA and annealing of oligo(dC)-tailed cDNA with oligo(dG)-tailed pBR322 were performed using standard technology. The annealed DNA was transformed into E. coli HB101 and plated directly onto nitrocellulose filters (Millipore, HATF; 0.45 µm) on L-agar plates containing tetracycline (15 µg/ml).

D. Identification of Ubiquitin cDNA

A number of cDNAs representing potentially light-regulated mRNAs were obtained by screening a cDNA library by differential hybridization. Several of these cDNAs were selected and further screened by RNA blot analysis to confirm light regulation. One CDNA clone, p6T7.2b1, while not representing a red-light regulated mRNA, was of interest because it hybridized with three poly(A)+ RNAs of different size and abundance. Nick translated p6T7.2b1 hybridized strongly with the 2100 nucleotide and 1600 nucleotide mRNAs, but only weakly with the 800 nucleotide transcript. However, hybridization of Northern blots with a single stranded $^{32}$p-labeled RNA generated by SP6 polymerase transcription of linearized pCA210, a plasmid constructed by subcloning the CDNA insert of p6T7.2b1 into pSP64, readily detected all three transcripts.

Since RNA-RNA hybrids are known to be more thermally stable than DNA-RNA hybrids, single stranded RNA probes rather than nick translated DNA probes were used in Northern blot hybridizations. Again, the 1600 base transcript was found to be about 3 fold less abundant than the 2100 base transcript as determined from Northern blots, regardless of whether the blot was hybridized with nick translated DNA or single strand RNA probes. The smallest transcript was about half as abundant as the 2100 base mRNA in blots hybridized with RNA probes.

Restriction fragments were subcloned into M13mp18 and/or mp19 and sequenced by the dideoxynucleotide chain termination method. Analysis of the sequence of the clone revealed a single long open reading frame of 818 bp terminating in a TAA stop codon. The National Biomedical Research Foundation library was searched using the D fast P program for protein sequences homologous with the deduced amino acid sequence. Greater than 95% homology was found between the deduced amino acid sequence of the maize cDNA clone and the sequences of bovine and human ubiquitin.

E. Genomic Library Construction and Screening

High molecular weight maize DNA was isolated from frozen maize seedlings. DNA was partially digested with Sau3A, size fractionated and cloned into the BamH1 sites of Charon 35 (Loenen et al. (1983) Gene 26:171–179). A library of about 2×10$^6$pfu was screened for recombinant phage containing sequences homologous to the ubiquitin cDNA clone by in situ plaque hybridization using a ubiquitin cDNA clone as a hybridization probe. Recombinant phage were purified from broth lysates and phage DNA was isolated using standard techniques. Restriction endonuclease digestions were carried out according to manufacturers' specifications.

F. Genomic Southern Blot Analysis

Isolated, high molecular weight maize DNA was digested with EcoR1, Hind111 and Sac1, fractionated on 0.7% agarose gels and the DNA fragments were transferred to Gene Screen Plus™ (DuPont). Filters were prehybridized for 6–8 h at 65° C. in 6XSSC (1XSSC=0.15 M NaCl, 0.025 M Na Citrate), 5X Denhardt's medium, 100 µg/ml denatured, sonicated Salmon DNA, 20 µg/ml polyadenylic acid, 10 mM disodium EDTA and 0.5% SDS. Filters were hybridized at 65° C. in fresh buffer with $^{32}$p labeled plasmid DNA (pCA210). Autoradiography was carried out at −80° C. using Kodak X-OMAT AR Film and one DuPont Cronex LightningPlus intensifying screen. In each digest, 8 to 10 restriction fragments hybridized with the nick translated pCA210 probe, suggesting that ubiquitin is coded by a small multigene family. Evidence that ubiquitin is encoded by a small multigene family has also been reported for Xenopus, barley and yeast.

Two or three fragments in each digest hybridized strongly with the probe, whereas the remainder of the fragments hybridized weakly. The differences in hybridization intensities may reflect different sequence homology such that the cDNA probe hybridizes preferentially to the gene from which it was derived.

Ubiquitin genes from yeast and Xenopus have been characterized and have six and at least twelve ubiquitin repeats, respectively. Maize genes corresponding to the three transcripts detected on Northern blots may have seven, five and one or two ubiquitin repeats in the 2.1, 1.6 and 0.8 kb mRNAs, respectively. The maize ubiquitin gene described in this invention codes for seven repeats. Thus, the difference in hybridization intensity observed on Southern blots may be a result of the restriction fragments containing a different number of ubiquitin repeats.

The ubiquitin cDNA clone did not contain EcoR1 and Hind111 sites. However, the maize ubiquitin genes may contain introns which are cut by the restriction endonucleases used in the genomic digests. This could result in ubiquitin exons being on different fragments and could account for the differential hybridization intensities observed in the Southern blots.

G. Ubiquitin Sequence Analysis and Transcription Start Site Analysis

Dideoxynucleotide chain termination sequencing was performed using Klenow fragments of DNA polymerase 1 (Boehringer Mannheim). A 1.85 kb Pst1 fragment of the genomic clone lambda 7.2b1 (see FIG. 1b) homologous to the cDNA clone p6T7.2b.1 and the 2 kb Pst1 fragment immediately upstream, termed AC3#9M13RF, were subcloned in both orientations into M13mp19. Recombinant phage RF DNA was prepared as for plasmid DNA. Unidirectional progressive deletion clones for sequencing both strands of these Pst1 fragments were prepared. Exonuclease 111 and Exonuclease V(1981)1(1981)1 were obtained from New England Biolabs and Bethesda Research Laboratories, respectively. Computer analysis of DNA sequences was performed using programs made available by the University of Wisconsin Genetics Computer Group.

The transcription start site of the ubiquitin gene and the 3' junction of the intron and exon in the 5' untranslated region of the gene were determined by S1 nuclease mapping. Fragments suitable for S1 probes were prepared as follows. The ubiquitin DNA was digested with either Bgl11 or Xho1. These were then labeled with $^{32}$p using gamma −$^{32}$p ATP (6000 Ci/mmole, New England Nuclear, Boston, Mass.) and T4 polynucleotide kinase (New England Biolabs). Subsequent digestion of the Bgl11 and Xho1 kinased fragments with Pst1 and EcoR1, respectively, generated a 946 bp Pst1-Bgl11 fragment and a 643 bp EcoR1-Xho1 fragment. These fragments were separated from the other end-labeled fragments by electrophoresis through a 5% polyacrylamide gel. Slices containing the 946 bp Pst1-Bgl11 and the 643 bp EcoR1-Xho1 fragments were cut out of the gel and the labeled DNAs were eluted from the gel. End-labeled DNA fragment (10–20 fmole) was hybridized with 2 µg of poly (A)+ RNA in 30 µl of buffer containing 80% deionized formamide, 0.4 M sodium chloride, 40 mM PIPES (pH6.4) and 1 mM EDTA (pH8.0). The nucleic acid solution was heated to 80° C. for 15 min to denature the DNA and then incubated at 42° C. for about 16 h. Ice-cold S1 digestion buffer (300 µl) containing 280 mM sodium chloride, 50 mM sodium acetate (pH4.6), 4.5 mM zinc sulfate and 20 µg/ml single stranded DNA was added and the DNA digested with 250 units/ml of S1 nuclease (New England Nuclear). The reaction was stopped with 75 µl of S1 termination mix containing 2.5 M ammonium acetate and 50 mM EDTA. The products of the S1 nuclease digestion were then separated on a 6% polyacrylamide/8 M urea gel and visualized by autoradiography. The end points of the S1 protected fragments in the ubiquitin sequence were determined by comparison with a sequence ladder generated by Maxam/Gilbert base modification-cleavage reactions carried out on the end labeled fragments used as S1 probes.

The DNA sequence of the maize ubiquitin-1 gene, lambda 7.2b1, is shown in FIG. 2. The sequence is composed of 899 bases upstream of the transcription start site, 1992 bases of 5' untranslated and intron sequences, and 1999 bases encoding seven ubiquitin protein repeats preceding 249 bases of 3' sequence. A "TATA" box is located at −30 and two overlapping heat shock elements are located at −214 and −204. The DNA sequence of the coding and 3' regions of the ubiquitin-1 gene from maize, lambda 7.2b1, is also presented in FIG. 3. The derived amino acid sequence of maize ubiquitin is shown at the top and the nucleotide sequence of the seven ubiquitin repeats is aligned underneath. A schematic of the organization of the seven complete ubiquitin units in the genomic DNA is shown in FIG. 1C.

Figure 3:
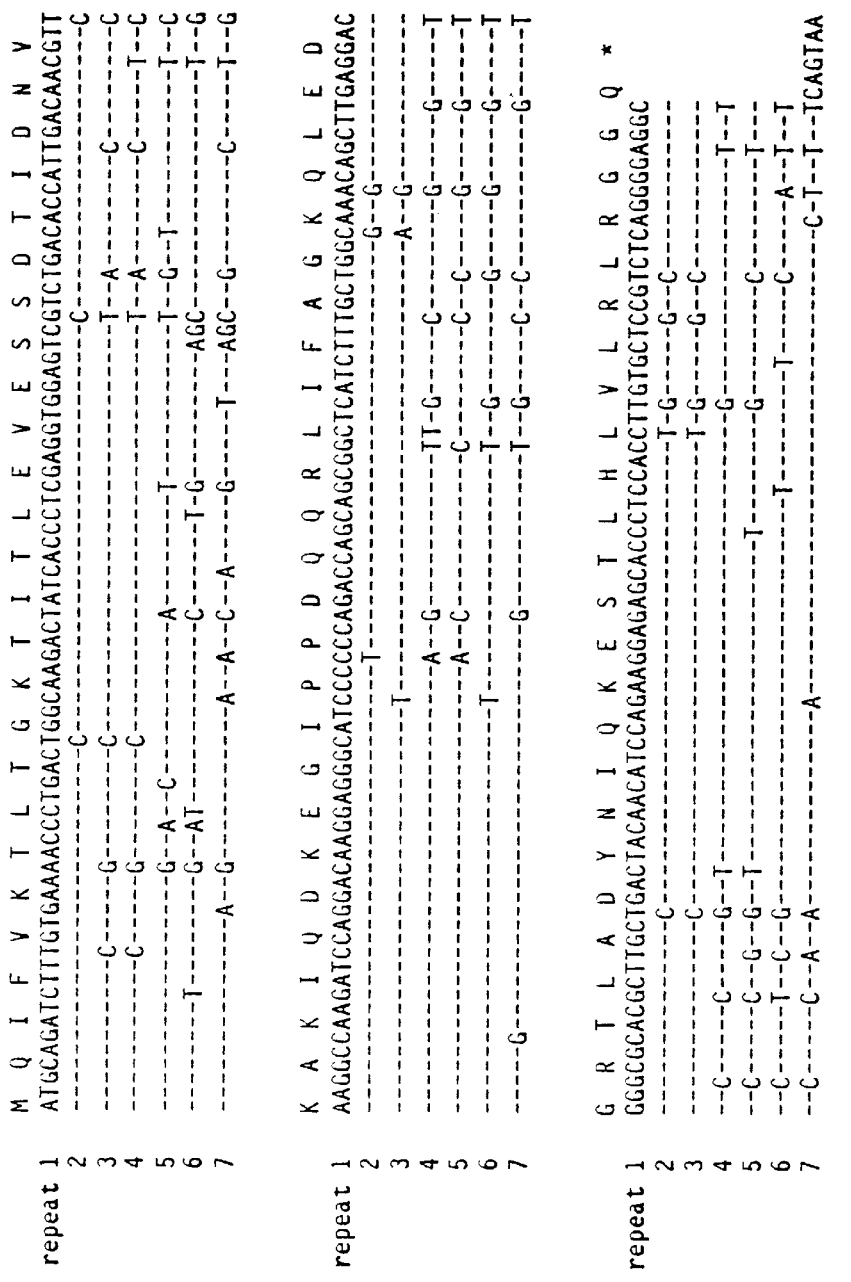
FIG. 3 demonstrates that all seven of the ubiquitin coding repeats encode an identical amino acid sequence. The nucleotide sequence of the seven repeats is shown aligned under the derived amino acid sequence. An additional 77th amino acid, glutamine, is present in the 7th repeat preceding the stop codon. A polyadenylation signal, AATAAT, is present in the 3' untranslated region, 113 bp from the stop codon.

The derived amino acid sequences of all of the ubiquitin repeats are identical (FIG. 3). The terminal (seventh) ubiquitin repeat contains an additional 77th amino acid, glutamine, prior to the TAA stop codon. This additional amino acid is not found in mature ubiquitin, and is apparently removed during processing. The 77th amino acid of the final repeat in the human gene is valine, while in the two chicken genes, it is tyrosine and asparagine. Yeast and barley also have an extra amino acid, asparagine and lysine, respectively; however, an extra amino acid was not found in the Xenopus gene. This extra amino acid has been proposed to function as a block to conjugation of unprocessed polyubiquitin to target proteins. A polyadenylation signal (5'-AATAAT3') is present in the 3' untranslated sequence, 113 bp from the stop codon.

All seven repeats encode the identical amino acid sequence, whereas the nucleotide sequence of the repeats varies by as many as 39 nucleotides. This is similar to what has been reported for the nucleotide sequence homologies between ubiquitin coding repeats of other ubiquitin genes. About 80% of the nucleotide mismatches between ubiquitin repeats are at the third (wobble) base in the codon. Alternate codon usage for leucine (5 codons), serine (3 codons) and arginine (3 codons) account for the remaining nucleotide mismatches.

The amino acid sequence for maize ubiquitin is identical to that determined for two other higher plants, oat and barley. The sequence differs from the sequence reported for yeast by two amino acids; alanine for serine substitutions at positions 28 and 57. The maize sequence is also slightly different from that reported for ubiquitin from all animals; substitutions by serine for proline at position 19, aspartate for glutamate at position 24 and alanine for serine at position 57. Thus, based on sequence, there appear to be three types of ubiquitin: plant, animal and yeast.

Example 2

Figure 4:
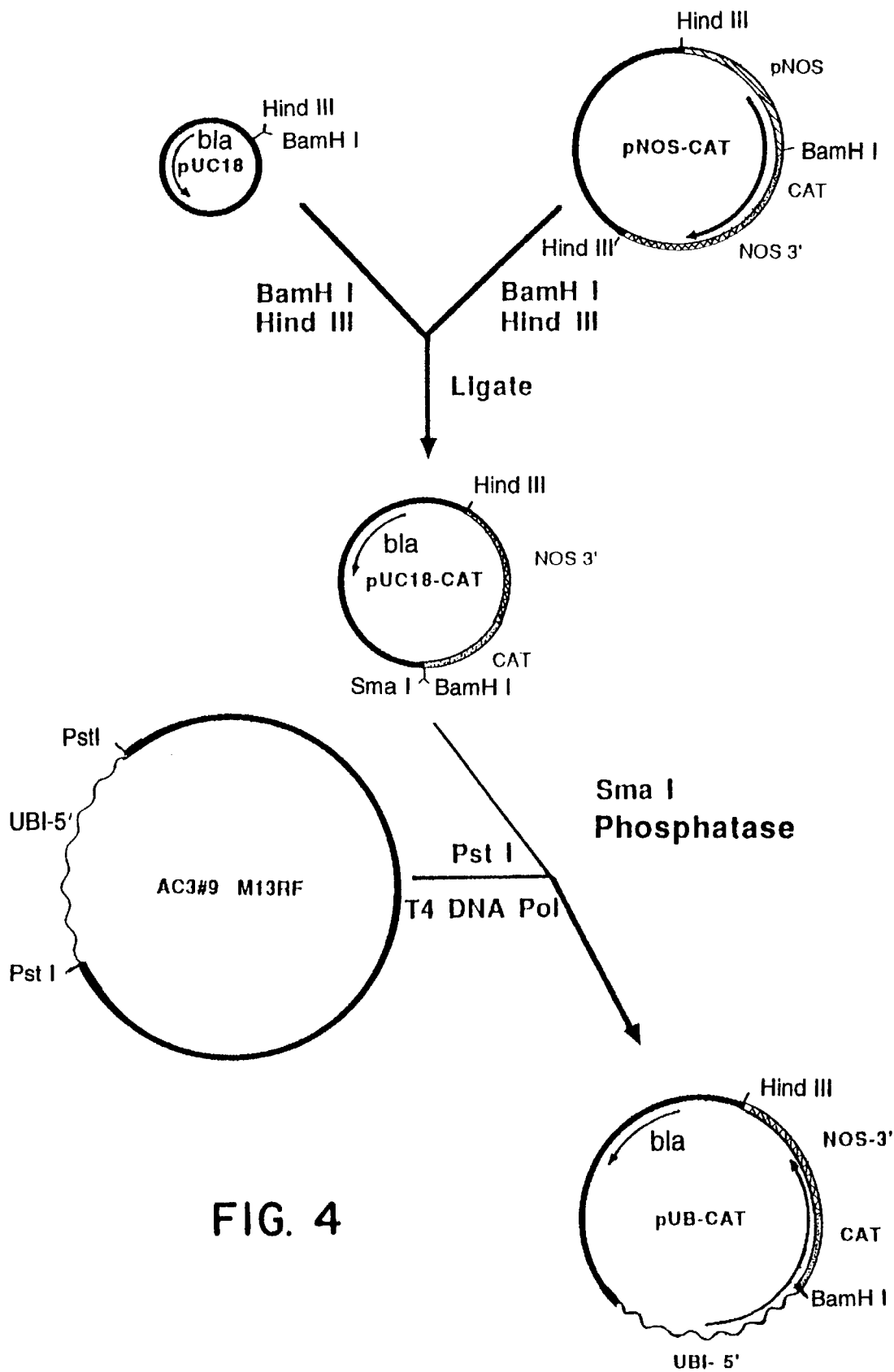
FIG. 4 is a diagrammatic presentation of the procedure used for the construction of the maize ubiquitin promoter region-chloramphenicol acetyl transferase (CAT) gene fusion.

Construction of Plasmid pUB-CAT Comprising the Maize Ubiquitin Promoter System and a Structural Gene A. Promoter isolation and construction of pUB-CAT The procedure used for construction of the ubiquitin gene upstream region-chloramphenicol acetyl transferase (CAT) gene fusion is outlined in FIG. 4. The BamH1-Hind111 restriction fragment containing the CAT gene and the nopaline synthase (NOS) 3' untranslated region and polyadenylation signal of PNOS-CAT (Fromm et al. (1985) Proc. Natl. Acad. Sci. 82:5824–5828) was subcloned into BamH1 and Hind111 digested pUC18. This construct was termed pUC18-CAT.

An approximately 2.0 kb Pst1 fragment immediately upstream of the ubiquitin polyprotein coding region of the maize ubiquitin gene lambda 7.2b1 was subcloned into M13mp19. This segment of DNA spans nucleotides −899 to 1092 of the maize ubiquitin sequence documented in FIG. 2. This recombinant DNA was termed AC3#9M13RF and contains the ubiquitin promoter, 5' untranslated leader sequence and about 1 kb intron, labeled UBI-5' in FIG. 4.

The ubiquitin promoter-CAT reporter gene fusion was constructed by blunt ending with $T_4$ DNA polymerase the 2.0 kb Pst1 fragment of AC3#9M13RF and cloning this fragment into Sma1-digested pUC18-CAT. This construct was termed pUB-CAT.

B. Introduction of Recombinant DNA into Oat and Tobacco Protoplast

Leaves (2 g) of 5- to 6- day old etiolated oat seedlings were finely chopped with a razor blade. The tissue was rinsed several times with digestion medium (3 mM MES, pH5.7, 10 mM calcium chloride, 0.5 M mannitol and 2 mg/ml arginine) and then incubated for 4 h at room temperature with 20 ml digestion medium containing 2% cellulase. The tissue was shaken occasionally to release protoplasts. The material was filtered through a 63 μm mesh and centrifuged 5 min at 50 xg. The supernatant fluid was removed and the protoplasts were washed two times with digestion medium and then resuspended in electroporation buffer to give 0.5 ml of protoplast suspension per electroporation. The electroporation buffer consisted of: 10 mM HEPES, pH7.2, 150 mM sodium chloride, 4 mM calcium chloride and 0.5 M mannitol.

Protoplasts (0.5 ml) in electroporation buffer were mixed on ice with 0.5 ml of electroporation buffer containing 40 μg plasmid DNA plus 100 μg sonicated salmon DNA. The protoplasts were electroporated on ice with a 350 volt, 70 msec pulse. The protoplasts were incubated another 10 min on ice, then diluted into 10 ml Murashige-Skoog (MS) medium and incubated at room temperature for 24 h.

Protoplasts were pelleted by centrifugation for 5 min at 50 xg. The supernatant fluid was removed and the protoplasts washed once with MS medium. The protoplast pellet was resuspended in 200 μl Buffer A (0.25 M Tris, pH7.8, 1 mM EDTA, 1 mM β-mercaptoethanol) and transferred to a microcentrifuge tube. Protoplasts were disrupted by sonication for 5–10 sec at the lowest setting. Protoplast debris was pelleted by centrifugation for 5 min at 4° C. The supernatant fluid was removed, heated to 65° C. for 10 min and stored at −20° C.

C. Assay for CAT Activity in Transformed Protoplasts

Aliquots (100 μl) of the electroporated protoplast extract (extract of cells transformed with recombinant DNA) were added to 80 μl of Buffer A and 20 μl of a mix of 20 μl $^{14}$C-chloramphenicol (40–60 mCi/mM), 2 mg acetyl CoA and 230 μl Buffer A. The reaction was incubated for 90 min at 37° C. The reaction products were extracted with 600 μl ethyl acetate and were concentrated by evaporating the ethyl acetate and resuspending in 10 μl ethyl acetate. The reaction products were separated by thin layer chromatography using chloroform:methanol (95:5,v/v) solvent and were detected by autoradiography.

Figure 5:
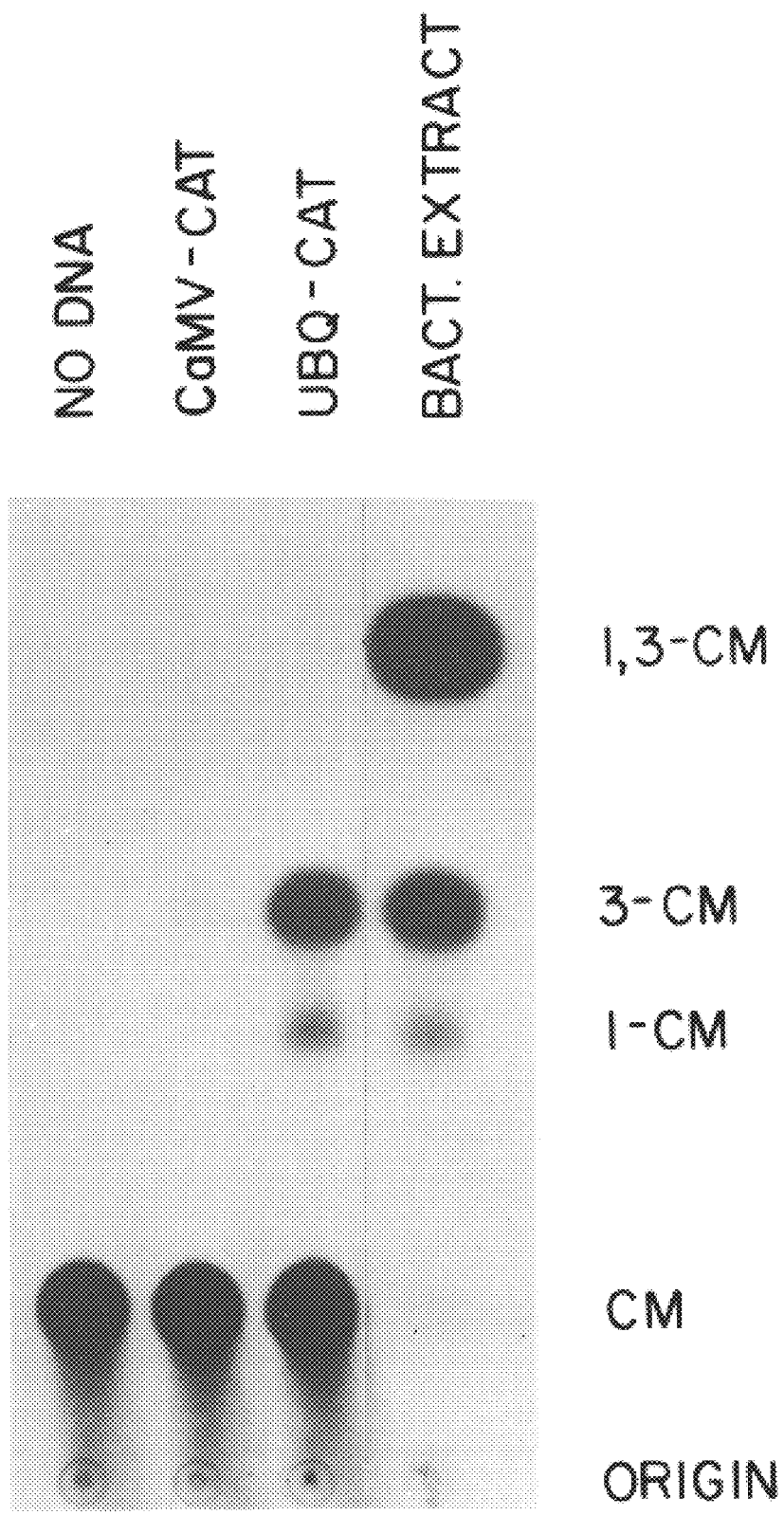
FIG. 5 presents an assay for the ubiquitin promoter. CaMV-CAT, cauliflower mosaic virus 35S promoter—CAT gene fusion; UBQ-CAT, maize ubiquitin promoter—CAT gene fusion.

Transformation of host cells was determined by measuring the amount of enzymatic activity expressed by the structural gene contained within the promoter-gene fusion construct. In this example, the structural gene encoding chloramphenicol acetyl transferase was employed in the DNA construct. To test the efficacy of the promoter utilized in the recombinant DNA fusion construct, parallel electroporations were carried out, utilizing either the maize ubiquitin promoter-CAT gene fusion pUC-CAT (described herein and in FIG. 4) and pCaMV-CAT, a cauliflower mosaic virus 35S promoter-CAT gene fusion (Fromm et al. (1985) Proc. Natl. Acad. Sci. USA 82:5824–5828) obtained from V. Walbot, Stanford University. As illustrated in FIG. 5, in oat protoplasts the ubiquitin promoter is "stronger" than the CaMV promoter, as judged by the amount of enzymatic activity expressed.

Example 3

Heat Shock Response

A. Heat Shock Treatment

To heat shock, 4 to 5 day old etiolated seedlings were transferred to an incubator at 42° C. and harvested 1, 3 and 8 h after transfer. Total RNA (7 μg) was isolated, denatured and electrophoresed through a 1.5% agarose 3% formaldehyde gel. The RNA was transferred to Gene Screen and probed with single stranded RNA transcribed from linearized pCA210 using SP6 RNA polymerase. (The recombinant plasmid, pCA210, was constructed by subcloning the 975 bp insert of p6T7.2bl into pSP64 (Promega) so that SP6 RNA polymerase synthesized a RNA probe specific for hybridization with ubiquitin mRNA.) After autoradiography, the bands were cut out and the amount of radioactivity bound to the filter was determined by liquid scintillation. From analysis of the Northern blots, levels of three ubiquitin transcripts were determined.

One hour after transfer to 42° C., the level of the 2.1 kb transcript increased 2.5 to 3 fold. An approximately 2 fold increase was observed for the 1.6 kb transcript, however, no increase was seen for the 0.8 kb transcript. By three hours after transfer of the seedlings to elevated temperature, the levels of the two largest ubiquitin transcripts had returned to the level observed in unshocked tissue and remained at those levels for at least another five hours. The transitory nature of ubiquitin during the heat shock response in maize may indicate that ubiquitin has a specialized role in heat shock and that only brief periods of increased levels of ubiquitin are required.

B. Heat Shock Sequences

The nucleotide sequence of the maize ubiquitin gene is presented in FIG. 2. Within the promoter region are nucleotide sequences homologous to the consensus heat shock sequence that has been shown to confer stress inducibility when placed upstream of heterologous promoters (Pelham (1982) supra). The consensus sequence for the Drosophila heat shock element is 5'-CTGGAATNTTCTAGA-3' where N=A, T, C, or G) (Support for this definition of N is found) and is generally found approximately 26 bases upstream of the transcriptional start site.

Located within 900 bases 5' to the transcriptional start site of the maize ubiquitin promoter are two overlapping heat shock sequences:

5'-CTGGA CCCCTCTCGA-3' starting at nucleotide −214, and

5'-CTCGA GAGTTCCGCT-3' starting at nucleotide −204.

The ubiquitin promoter from chicken embryo fibroblasts was also found to contain two overlapping heat shock consensus promoter sequences:

5'-CTCGA ATCTTCCAG-3' starting at nucleotide −369, and

5'-CCAGA GCTTTCTTTT-3' starting at nucleotide −359. The 5' flanking region of the yeast ubiquitin gene UB14 (E. Ozkaynak et al. (1987) supra) comprises an 18 kb, rotationally symmetric (palindromic) sequence, 5'-TTCTAGAACGTTCTAGAA-3', 365 bases upstream of the translation start site. The middle 14 bases (underlined) of this 18 bp sequence contain an exact homology to the rotationally symmetric consensus 'heat shock box' nucleotide sequence starting at approximately 284 nucleotides upstream of the presumed transcription start site.

The relative position of the heat shock sequence with respect to the transcriptional initiation codon and its ultimate consequence on the magnitude of the induction response to heat shock or other stress remains largely unknown, although it has been suggested (U. Bond and M. Schlesinger (1986) supra) that the further a heat shock element is located 5' from the transcriptional start site, the smaller is the level of induction in response to stress.

In this invention it is assumed that a heat shock sequence may be arbitrarily positioned at different loci within the ubiquitin promoter and that it may be chemically altered in sequence or be replaced with a synthetic homologous sequence, so long as the modified promoter sequence retains ubiquitin promoter function, which comprises the initiation, direction and regulation of transcription under stress and non-stress conditions. Biochemical techniques required to insert and/or delete nucleotides and to manipulate the resultant DNA fragments are well known to those skilled in the art of genetic redesigning.

Example 4

Presence of Heat Shock Sequence(s) and a Large Intron Within the Ubiquitin Promoter System The ubiquitin promoter system from maize is characterized structurally by the presence of two overlapping heat shock sequences approximately two hundred bp upstream of the transcriptional start site and that of a large (approximately 1 kb) intron between the transcriptional start site and the translational initiation codon. This promoter structure is very similar to that reported (U. Bond et al. (1986) supra) for the ubiquitin promoter from chicken embryo fibroblasts in which two overlapping heat shock sequences are located approximately 350 bp upstream of the transcriptional start site and a 674 bp intron is contained between the transcriptional and translational initiation codons. Recently (E. Ozkaynak et al. (1987) supra), the nucleotide sequence of the promoter region from yeast ubiquitin UB14 gene was determined and found to contain a heat shock sequence approximately 280 bp upstream of the transcriptional start site, but this yeast ubiquitin promoter was devoid of a large intron between the transcription and translation initiation sites. However, two other yeast ubiquitin genes, which did contain introns, were found to be lacking sequences homologous to the Pelham "heat shock box" sequence.

Ubiquitin promoters have been shown to up-regulate expression of ubiquitin in response to heat shock in yeast, chicken embryo fibroblasts and maize. In all three systems, the level of ubiquitin mRNA is elevated after heat shock treatment and the increase in ubiquitin level was determined in maize and chicken embryo fibroblasts to be approximately 3 fold. This enhancement in ubiquitin expression in response to heat shock is significantly less than that obtained with other heat shock genes. It was found in chicken embryo fibroblasts that the levels of ubiquitin MRNA in cells exposed to 45° C. increased by 2.5 fold over a 2.5 h period, whereas the levels of HSP70 mRNA increased 10 fold under the same heat shock conditions. Moreover, the relative instability of ubiquitin mRNA during recovery of cells from a 3 h heat shock (half-life of approximately 1.5 to 2 h) was also found to differ significantly from that of HSP70 mRNAs which were found to be stable.

It is interesting to note that in contrast to ubiquitin promoters, HSP70 genes do not contain large introns between the transcriptional and translational initiation codons. Another difference between the ubiquitin promoter and other heat shock promoters is that ubiquitin is expressed both constitutively and inductively, whereas expression of classical heat shock proteins occurs predominantly in response to heat shock or other stress. This invention allows skilled workers knowledgeable in the art to modify ubiquitin promoter with respect to the composition/sequence and position of both the intron and the heat shock sequences in order to alter constitutive and/or inductive expression of ubiquitin. Also, standard recombinant technology may be employed to reposition, as well as to chemically alter the nucleotide sequences within the maize ubiquitin promoter region in such a fashion as to retain or improve the promoter function of the resultant modified DNA. Testing for ubiquitin promoter function may be carried out as taught in example 2.

We claim:

1. A DNA construct comprising:

(a) a DNA sequence no larger than 2 kb, said DNA sequence comprising a plant ubiquitin regulatory system, wherein said regulatory system contains a heat shock element and an intron, said intron being located at 3' to said heat shock element, and (b) a plant-expressible structural gene wherein said structural gene is placed under the regulatory control of said plant ubiquitin regulatory system.

* * * * *

UNITED STATES PATENT AND TRADEMARK OFFICE
CERTIFICATE OF CORRECTION

PATENT NO. : 6,020,190
DATED : Feb. 1, 2000
INVENTOR(S) : Quail, et al

Page 1 of 2

It is certified that error appears in the above-identified patent and that said Letters Patent is hereby corrected as shown below:

Column 3, line 62: "size (1981)-(1981).distribution" should read --size distribution--.

Column 5, line 31: "zein (1981) mRNA" should read --zein mRNA--.

Column 6, line 36: "5°" should read --5'--.

Column 6, line 49: "5°" should read --5'--.

Column 6, line 50: "3°" should read --3'--.

Column 6, line 51: "5°" should read --5'--.

Column 7, line 58: "not:" should read --not--.

Column 8, lines 14&15: "the(1981)-(1981)-transcription" should read --the transcription--.

Column 8, lines 36&37: "some(1981).variation" should read --some variation--.

Column 10, line 22: "CTGGAATNTTCTAGE" should read --CTGGAATNTTCTAGA--

Column 11, line 19: "An exon" should read --An untranslated exon--.

UNITED STATES PATENT AND TRADEMARK OFFICE
CERTIFICATE OF CORRECTION

PATENT NO. : 6,020,190
DATED : Feb. 1, 2000
INVENTOR(S) : Quail, et al

It is certified that error appears in the above-identified patent and that said Letters Patent is hereby corrected as shown below:

Column 14, line 2: "CDNA" should read --cDNA--.

Column 14, line 13: "CDNA" should read --cDNA--.

Column 14, line 22: "CDNA" should read --cDNA--.

Column 15, line 46: "V(1981)I(1981)I were" should read --VII were--.

Column 17, line 11: "PNOS-CAT" should read --pNOS-CAT--.

Column 17, line 14: "pUC18" should read --puC18--.

Column 20, line 26: "MRNA" should read --mRNA--.

Signed and Sealed this

Thirteenth Day of February, 2001

*Attest:*

NICHOLAS P. GODICI

*Attesting Officer*   Acting Director of the United States Patent and Trademark Office